(12) United States Patent
Hugghins et al.

(10) Patent No.: US 10,845,354 B2
(45) Date of Patent: Nov. 24, 2020

(54) SYSTEM FOR SIMULATING IN SITU DOWNHOLE DRILLING CONDITIONS AND TESTING OF CORE SAMPLES

(71) Applicant: NEWPARK DRILLING FLUIDS, LLC, The Woodlands, TX (US)

(72) Inventors: Joel Franklin Hugghins, The Woodlands, TX (US); Robert Patterson, The Woodlands, TX (US); William Thrasher, The Woodlands, TX (US); David Ghobar, The Woodlands, TX (US); Samir Harmad Sharf-Aldin, The Woodlands, TX (US); Munir Hamad Sharf-Aldin, The Woodlands, TX (US)

(73) Assignee: Newpark Drilling Fluids LLC, The Woodlands, TX (US)

( * ) Notice: Subject to any disclaimer, the term of this patent is extended or adjusted under 35 U.S.C. 154(b) by 0 days.

(21) Appl. No.: 16/367,970

(22) PCT Filed: May 21, 2018

(86) PCT No.: PCT/US2018/033688
§ 371 (c)(1),
(2) Date: Mar. 28, 2019

(87) PCT Pub. No.: WO2019/226149
PCT Pub. Date: Nov. 28, 2019

(65) Prior Publication Data
US 2019/0383786 A1    Dec. 19, 2019

(51) Int. Cl.
*G01N 33/24* (2006.01)
*G01N 15/08* (2006.01)
(Continued)

(52) U.S. Cl.
CPC ........... *G01N 33/24* (2013.01); *E21B 49/005* (2013.01); *G01N 3/18* (2013.01); *G01N 15/0826* (2013.01);
(Continued)

(58) Field of Classification Search
CPC ............ G01N 3/12; G01N 3/16; G01N 3/165; G01N 2203/0256; G01N 2203/0037;
(Continued)

(56) References Cited

U.S. PATENT DOCUMENTS 2,983,159 A * 5/1961 Zeligowsky ............. G01N 3/16
74/89.28
3,055,224 A * 9/1962 MacGeorge ............. G01N 3/16
74/420
(Continued)

FOREIGN PATENT DOCUMENTS

CN    103806907 A  *  5/2014
CN    107478516 A  * 12/2017  ............... G01N 3/12
(Continued)

OTHER PUBLICATIONS

Fuchs et al, Coriolis Mass Flow Meter With Direct Viscosity Measurement 2003 (Year: 2003).*
(Continued)

*Primary Examiner* — David L Singer
(74) *Attorney, Agent, or Firm* — Jones Delflache LLP; Marc L. Delflache

(57) ABSTRACT

A system for simulating in situ drilling and treatment conditions on a core sample from a subterranean formation. The system re-creates various subterranean loads and temperatures on a test sample representative of actual in situ conditions from the particular formation while a test structure within the system performs drilling activities on the core sample using drilling and treating under evaluation for
(Continued)

use in the particular subterranean formation. Thus, the impact on selected drilling and treating fluids can be evaluated as well as the impact those fluids had on a sample from the subterranean formation under in situ conditions.

58 Claims, 20 Drawing Sheets

(51) Int. Cl.
  *G01N 33/28* (2006.01)
  *G01N 3/18* (2006.01)
  *E21B 49/00* (2006.01)
  *G01N 29/04* (2006.01)
  *G01F 1/84* (2006.01)

(52) U.S. Cl.
  CPC ........... *G01N 33/2823* (2013.01); *G01F 1/84* (2013.01); *G01N 29/043* (2013.01); *G01N 2203/0003* (2013.01); *G01N 2203/0019* (2013.01); *G01N 2203/0037* (2013.01); *G01N 2203/0048* (2013.01); *G01N 2203/0057* (2013.01); *G01N 2203/0246* (2013.01); *G01N 2203/0256* (2013.01); *G01N 2203/0266* (2013.01); *G01N 2203/0623* (2013.01); *G01N 2203/0658* (2013.01); *G01N 2203/0676* (2013.01); *G01N 2203/0682* (2013.01); *G01N 2291/0289* (2013.01); *G01N 2291/044* (2013.01)

(58) Field of Classification Search
  CPC ............ G01N 2203/0246; B30B 1/181; B30B 1/186; B30B 9/3064; B30B 15/0023–0029; B30B 15/14–148; B29C 43/32; B29C 43/3272
  USPC ............. 73/817, 38, 152.07, 152.09, 152.11, 73/865.6, 153, 53.05; 100/289, 290, 178, 100/226–229 A
  See application file for complete search history.

(56) References Cited

U.S. PATENT DOCUMENTS

| | | | |
|---|---|---|---|
| 3,203,232 A * | 8/1965 | Lehnig, Jr. | G01N 3/16 73/796 |
| 3,616,685 A * | 11/1971 | Strom | G01N 3/02 73/84 |
| 4,791,822 A * | 12/1988 | Penny | E21B 43/267 73/38 |
| 5,265,461 A * | 11/1993 | Steiger | G01N 29/07 73/38 |
| 5,493,226 A | 2/1996 | Honarpour | |
| 5,616,842 A * | 4/1997 | Armengaud | G01N 11/14 73/152.18 |
| 5,868,030 A * | 2/1999 | Brumley | G01B 5/30 73/784 |
| 5,969,227 A * | 10/1999 | Kenney | G01N 19/02 73/10 |
| 6,055,874 A * | 5/2000 | Onan | E21B 49/00 73/865.6 |
| 6,084,826 A | 7/2000 | Leggett | |
| 6,088,294 A | 7/2000 | Leggett | |
| 6,305,265 B1 * | 10/2001 | Bingham | F04B 15/08 277/452 |
| 6,581,010 B2 | 6/2003 | Dubinsky | |
| 6,612,382 B2 | 9/2003 | King | |
| 6,772,066 B2 | 8/2004 | Cook | |
| 6,832,158 B2 | 12/2004 | Mese | |
| 7,278,496 B2 | 10/2007 | Leuchtenberg | |
| 7,861,609 B2 | 1/2011 | Haggerty | |
| 7,908,034 B2 | 3/2011 | Gray | |
| 7,953,587 B2 | 5/2011 | Bratton | |
| 8,014,987 B2 | 9/2011 | Pabon | |
| 8,271,243 B2 | 9/2012 | Koutsabeloulis | |
| 8,280,709 B2 | 10/2012 | Koutsabeloulis | |
| 8,301,426 B2 | 10/2012 | Abasov | |
| 8,423,337 B2 | 4/2013 | Hsu | |
| 8,548,782 B2 | 10/2013 | Hsu | |
| 8,683,858 B2 | 4/2014 | Piri | |
| 8,694,297 B2 | 4/2014 | Ding | |
| 8,725,477 B2 | 5/2014 | Zhang | |
| 8,762,118 B2 | 6/2014 | Nasreldin | |
| 8,775,141 B2 | 7/2014 | Raphael | |
| 8,818,777 B2 | 8/2014 | Howell | |
| 8,849,637 B2 | 9/2014 | Chavez | |
| 8,949,098 B2 | 2/2015 | King | |
| 9,097,103 B2 | 8/2015 | Pop | |
| 9,103,191 B2 | 8/2015 | Chapman | |
| 9,164,194 B2 | 10/2015 | Hsu | |
| 9,171,109 B2 | 10/2015 | Hegazy | |
| 9,322,259 B2 | 4/2016 | Kulathu | |
| 9,405,867 B2 | 8/2016 | Xia | |
| 9,470,052 B2 | 10/2016 | Edbury | |
| 9,506,305 B2 | 11/2016 | Leuchtenberg | |
| 9,506,336 B2 | 11/2016 | Thot | |
| 9,989,512 B2 | 6/2018 | Haggerty | |
| 2001/0050006 A1 * | 12/2001 | Nakamura | B30B 9/065 100/37 |
| 2004/0220742 A1 | 11/2004 | Mese et al. | |
| 2005/0150273 A1 * | 7/2005 | Potter | G01N 3/10 73/38 |
| 2009/0241700 A1 | 10/2009 | Haggerty et al. | |
| 2010/0088076 A1 | 4/2010 | Koutsabeloulis | |
| 2011/0271751 A1 * | 11/2011 | Brooks | E21B 43/11 73/152.07 |
| 2012/0211089 A1 | 8/2012 | Piri et al. | |
| 2013/0125630 A1 * | 5/2013 | Collins | E21B 43/20 73/64.56 |
| 2014/0007667 A1 * | 1/2014 | Haggerty | E21B 49/00 73/152.11 |
| 2014/0041941 A1 | 2/2014 | Edbury | |
| 2014/0291023 A1 | 10/2014 | Edbury | |
| 2014/0366620 A1 | 12/2014 | Haggerty | |
| 2015/0211350 A1 | 7/2015 | Norman | |
| 2016/0025884 A1 | 1/2016 | Difoggio | |
| 2016/0146653 A1 | 5/2016 | Skelding | |
| 2017/0009543 A1 | 1/2017 | Lovorn | |
| 2018/0045704 A1 * | 2/2018 | Al-Otaibi | G01N 15/082 |
| 2018/0335374 A1 * | 11/2018 | Kanj | E21B 49/006 |

FOREIGN PATENT DOCUMENTS

| | | | | |
|---|---|---|---|---|
| JP | 10277796 A | * | 10/1998 | ......... B30B 15/0094 |
| KR | 2001084984 A | * | 9/2001 | ............. G01N 3/165 |

OTHER PUBLICATIONS

Gray, Some rock mechanics aspects of petroleum engineering, ARMA-67-0405 The 9th U.S. Symposium on Rock Mechanics (USRMS), Apr. 17-19, Golden, Colorado (Year: 1967).*
Salisbury, Wellbore instability of shales using a downhole simulation test cell, ARMA-91-1015 Rock Mechanics as a Multidisciplinary Science Roegiers (ed), 1991 Balkerna, Rotterdam ISBN906191 194X (Year: 1991).*
Simpson et al, Downhole Simulation Cell Shows Unexpected Effects of Shale Hydration on Borehole Wall, SPE Drilling Engineering, Mar. 1989 (Year: 1989).*
Khademi, Thesis: Laboratory study of the effect of axial compliance on rock penetration of pdc bits, Master of Engineering Faculty of Engineering and Applied Science Memorial University Oct. 2014 (Year: 2014).*
Bikic et al, Liquid Viscosity Determination by Coriolis Flow Meter, Journal on Processing and Energy in Agriculture 14 (2010) (Year: 2010).*
Jenks et al, Fluid Flow Within a Porous Near a Diamond Core Medium Bit, 19th Annual Technical Meeting, The Petroleum. Society of CIM, Calgary, May 1968, The Journal of Canadian Petroleum (Year: 1968).*

(56) References Cited

OTHER PUBLICATIONS

Oort, A novel technique for the investigation of drilling fluid induced borehole instability in shales, presentation at the SPE/ISRM Rock Mechanics in Petroleum Engineering Conference held in Delft, The Netherlands, Aug. 29-31, 1994 (Year: 1994).*

Young Jr. et al, Dynamic Filtration During Microbit Drilling, Journal of Petroleum Technology, Sep. 1967 (Year: 1967).*

Ledgerwood et al, Bit Balling and Wellbore Instability of Downhole Shales, SPE 22578 presentation at the 66th Annual Technical Conference and Exhibition of the Society of Petroleum Engineers held in Dallas, TX, Oct. 6-9, 1991. (Year: 1991).*

Testing Techniques for Rock Mechanics, a symposium presented at the Fifth Pacific Area National Meeting American Society for Testing and Materials Seattle, Wash., Oct. 31-Nov. 5, 1965, ASTM Special Technical Publication No. 402 (Year: 1965).*

Andersen et al, PDC.Bit Performance Under Simulated Borehole Conditions, SPE Drilling & Completion. Sep. 1993 (Year: 1993).*

Ba, Thesis: Contribution to the monitoring of a drilling process tanker, Apr. 15, 2010 (Year: 2010).*

Machine Translation CN107478516A (Year: 2019).*

Machine Translation KR 2001084984 A (Year: 2019).*

* cited by examiner

SYSTEM FOR SIMULATING IN SITU DOWNHOLE DRILLING CONDITIONS AND TESTING OF CORE SAMPLES

FIELD OF THE INVENTION

The present invention relates to a system for simulating downhole drilling conditions. More particularly, the present invention relates to a system for simulating an in situ drilling environment under a variety of downhole conditions to determine the impact on a subterranean formation using selected drilling and treating fluids and to evaluate a subterranean rock formation.

BACKGROUND OF THE INVENTION

Simulating actual temperatures and pressures in a subterranean formation thousands of feet below ground surface or the seabed has always been a difficult task. In particular, the testing of selected drilling and treating fluids on a core sample extracted from a deep subterranean formation under the same in situ conditions the sample came from is a challenge. The challenge arises in accurately and simultaneously simulating the various forces that the core sample experiences in the selected formation. Such testing is further challenged due to the extreme temperatures the subject formation experiences during the drilling operation.

Testing facilities in the past have attempted to replicate one or more selected variables, but all the various forces have not been replicated, resulting in the need to extrapolate other possible forces and the impact of very elevated temperatures (over 350° F.). Thus, the resulting impact on the fluid being tested as well as the core sample has not been a thorough in situ test of all the forces and very elevated temperatures. Additionally, the testing of multiple types of drilling or treating fluids, concurrently or sequentially, in the same operation has not been possible.

The prior art systems have been primarily qualitative measuring tools rather than a scalable in situ quantitative measuring system. The challenge exists because of the need to subject the core sample to a combined series of in situ pressures from various sources while concurrently exposing the sample and associated fluids to significant elevated temperatures. With an in situ quantitative measuring system, it would be possible to subject the core sample to a variety of drilling fluids and treating fluids to determine the impact the fluids have on the selected subterranean formation and provide the operator with a unique formulation of fluids to achieve the intended purpose of a particular drilling or treating operation in an effort to produce hydrocarbons from an existing formation or to improve production from an existing well.

Therefore, the need exists for an improved simulation system which can subject the core sample to realistic, real-time, in situ conditions of pressure and temperature while evaluating the performance of selected drilling and treating fluids on the particular formation during simultaneous drilling. Additionally, the system should be capable of measuring the impact of extreme conditions on a rock formation that may not be subjected to the use of a drilling or treating fluid but the impact of other extreme conditions.

SUMMARY OF THE INVENTION

The present invention is a system for simulating in situ subterranean formation conditions and, preferably, the testing and measuring the performance of a drilling or treating fluid on a core sample from the selected subterranean formation. Preferably, the present invention comprises a source of fluid and a motor assembly to circulate the fluid within the system. A first pressure source is included to generate a pressure which is representative of the overburden pressure of the subterranean formation. As used herein, the term "overburden" means the influence of the geological formation above the point of measurement taking into account the load caused by the weight of the formation including fluids above the point of measurement in an orthogonal direction—i.e. x, y, z directions. A second pressure source is also included to generate a pressure representative of the pressure exerted on the pores of the sample from the subterranean formation. A third pressure source is included to generate a pressure representative of the confining pressure exerted laterally on the sample from the subterranean formation. The present invention includes a transfer assembly to impose substantially the same pressure on the drilling/treating fluid as generated by the first pressure source. A first measuring source is included to detect selected properties of the fluid prior to testing. The present invention also includes a test structure having a frame, a test chamber supported within the frame to support the sample, and a drilling assembly to drill a borehole into the sample using the potentially heated or cooled fluid to circulate around a drill-bit within the sample. The test structure subjects the sample to the same pressures as established by the first, second, and third sources. A second measuring sources is also included to detect selected properties of the fluid following testing. The invention includes a processor to compare the results of the first measuring source with the results of the second measuring source to determine the impact of the simulated drilling activity on the characteristics of the fluid and the impact of the fluid and simulated drilling activity on the core sample.

In an alternate embodiment, the present invention is a system for simulating in situ subterranean formation conditions and testing and measuring the performance of a drilling or treating fluid on a core sample from the selected subterranean formation. The present invention comprises a source for the fluid and motor assembly to circulate the fluid within the system. A first measuring source is included to detect selected properties of the fluid prior to testing, and a plurality of pressure sources are also included to generate a pressure representative of the overburden pressure of the subterranean formation, a pressure representative of the pressure exerted on the pores of the sample from the subterranean formation, and a pressure representative of the confining pressure exerted laterally on the sample from the subterranean formation. The invention includes a transfer assembly to impose substantially the same overburden pressure on the fluid as generated by at least one of the pressures sources. At least one heater is used to optionally heat the fluid as it advances through the system to a preselected temperature. Alternatively, a chiller or other heat exchanger may be used to cool the sample or fluids. The invention also includes a test structure having a frame, a test chamber supported within the frame to support the sample, and a drilling assembly to drill a borehole in the sample using the heated fluid to circulate the bit within the sample. The test structure subjects the sample to the same pressures as established by the plurality of pressure sources. The present invention also includes a second measuring source to detect selected properties of the fluid following testing. A plurality of sensors are included to measure various selected properties of the sample and events that occur during testing. The invention also includes a processor to compare the results from the first measuring source and the second measuring source to determine the impact of the simulated drilling activity on the fluid and of the fluid and simulated drilling on the sample.

In yet another alternate embodiment, the present invention is a system for simulating in situ subterranean rock formation conditions and testing and measuring the impact of extreme conditions on a core sample from the selected subterranean formation. The present invention comprises a source for the fluid and motor assembly to circulate the fluid within the system. A first measuring source is included to detect selected properties of the fluid prior to testing, and a plurality of pressure sources are also included to generate a pressure representative of the overburden pressure of the subterranean formation, a pressure representative of the pressure exerted on the pores of the sample from the subterranean formation, and a pressure representative of the confining pressure exerted laterally on the sample from the subterranean formation. The invention includes a transfer assembly to impose substantially the same overburden pressure on the fluid as generated by at least one of the pressures sources. At least one heater is used to optionally heat the fluid as it advances through the system to a preselected temperature. Alternatively, a chiller may be used to cool the sample or fluids. The invention also includes a test structure having a frame, a test chamber supported within the frame to support the sample, and a drilling assembly to drill a borehole in the sample using the heated fluid to circulate the bit within the sample. The test structure subjects the sample to the same pressures as established by the plurality of pressure sources. The present invention also includes a second measuring source to detect selected properties of the fluid following testing. A plurality of sensors are included to measure various selected properties of the sample and events that occur during testing. The invention also includes a processor to compare the results from the first measuring source and the second measuring source to determine the impact of the simulated drilling activity on the fluid and of the fluid and simulated drilling on the sample.

The method of the present invention is measuring the impact of a simulated drilling activity using drilling and treating fluids on a core sample from a subterranean formation, within a testing system. The method comprises providing a fluid and circulating the fluid within the testing system. The method also comprises measuring selected properties of the fluid prior to testing and heating the fluid to a predetermined testing temperature. The method also includes pressurizing the fluid to a pressure representative of the overburden pressure of the subterranean formation. The method of the present invention subjects the sample to the overburden of the subterranean formation. Concurrently, the method subjecting the sample to a laterally confining pressure at substantially the same pressure that the fluid is subjected. Additionally, the invention concurrently subjects the sample to a pore pressure at substantially the same pressure that the fluid is subjected. The method also includes measuring selected properties of the sample during testing and measuring selected properties of the fluid following testing. The method of the present invention also processes the measured properties from the sample during testing and the fluid following testing to determine the impact of the simulated drilling activity on the fluid and the sample.

The more important features of the present invention have been described rather broadly in order that the detailed description may be better understood. There are, of course, additional features of the present invention which will be described hereinafter and which will also form the subject of the claims appended hereto.

DESCRIPTION OF THE DRAWINGS

In order to more fully describe the drawings used in the detailed description of the present invention, a description of each figure is provided.

DETAILED DESCRIPTION OF THE INVENTION

Figure 1:
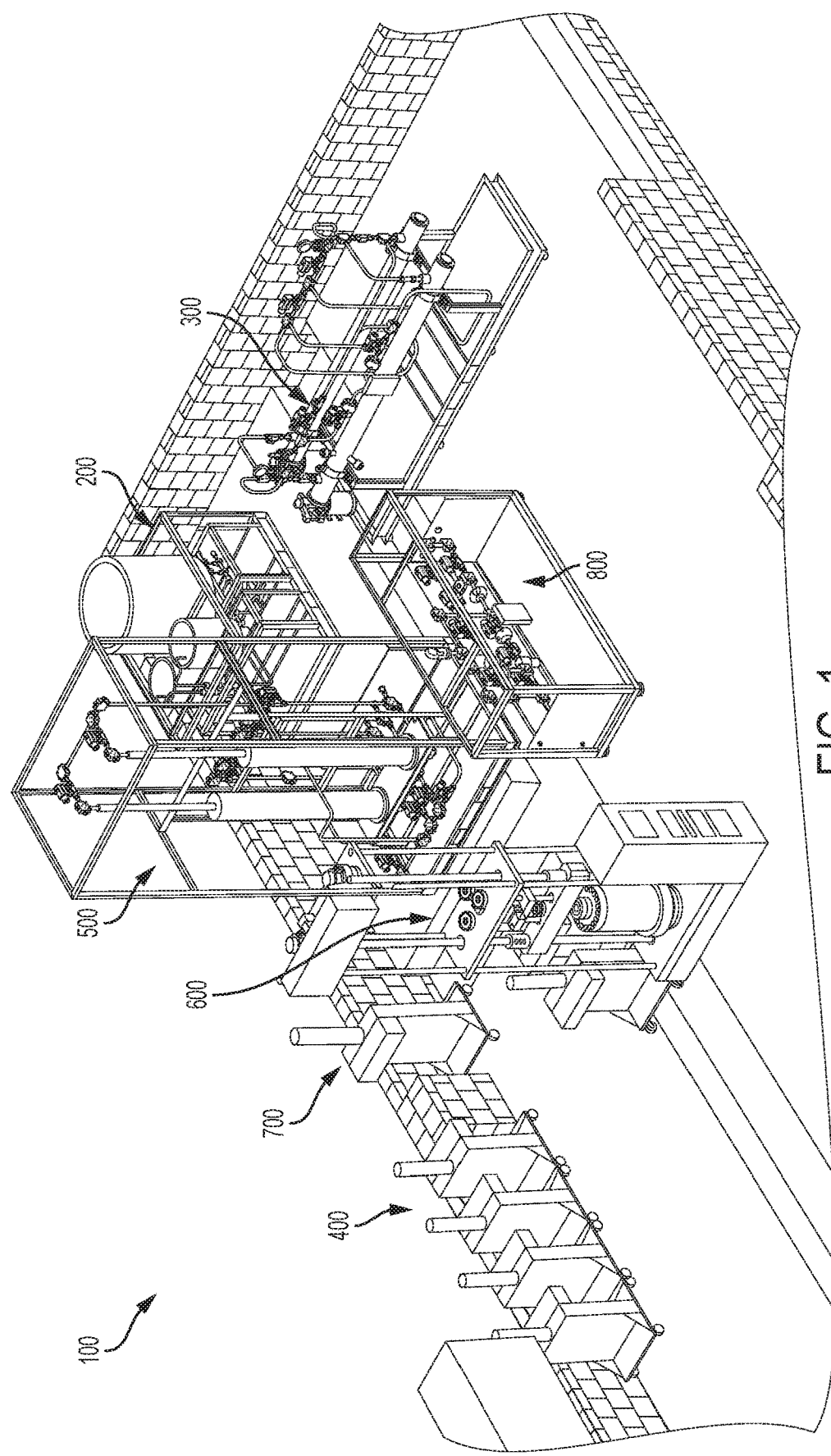
FIG. 1 is a perspective view of the present invention.

Characteristics and advantages of the present disclosure and additional features and benefits will be readily apparent to those skilled in the art upon consideration of the following detailed description of exemplary embodiments of the present disclosure and referring to the accompanying figures. It should be understood that the description herein and appended drawings, being of example embodiments, are not intended to limit the claims of this patent or any patent or patent application claiming priority hereto. On the contrary, the intention is to cover all modifications, equivalents and alternatives falling within the spirit and scope of the claims.

Many changes may be made to the particular embodiments and details disclosed herein without departing from such spirit and scope.

In showing and describing preferred embodiments in the appended figures, common or similar elements are referenced with like or identical reference numerals or are apparent from the figures and/or the description herein. The figures are not necessarily to scale and certain features and certain views of the figures may be shown exaggerated in scale or in schematic in the interest of clarity and conciseness.

As used herein and throughout various portions (and headings) of this patent application, the terms "disclosure", "present disclosure" and variations thereof are not intended to mean every possible embodiment encompassed by this disclosure or any particular claim(s). Thus, the subject matter of each such reference should not be considered as necessary for, or part of, every embodiment hereof or of any particular claim(s) merely because of such reference.

Certain terms are used herein and in the appended claims to refer to particular components. As one skilled in the art will appreciate, different persons may refer to a component by different names. This document does not intend to distinguish between components that differ in name but not function. Also, the terms "including" and "comprising" are used herein and in the appended claims in an open-ended fashion, and thus should be interpreted to mean "including, but not limited to . . . ." Further, reference herein and in the appended claims to components and aspects in a singular tense does not necessarily limit the present disclosure or appended claims to only one such component or aspect, but should be interpreted generally to mean one or more, as may be suitable and desirable in each particular instance.

Figure 2:
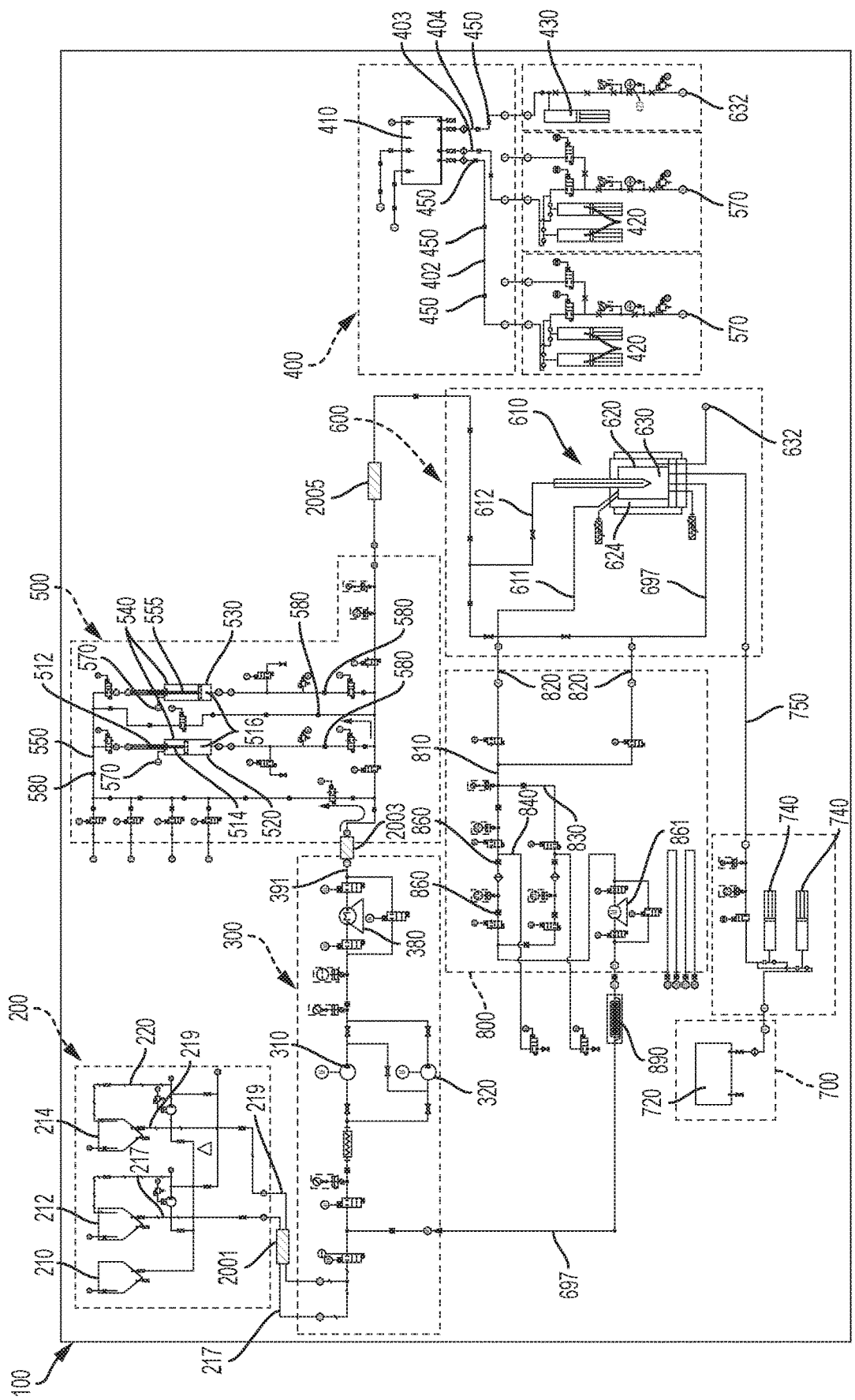
FIG. 2 is a schematic of the present invention.

Referring now to FIGS. 1-2, a drilling simulation system is shown capable of simulating a variety of downhole conditions on a core sample extracted from a given subterranean formation. The sample may be a single core removed from a particular formation or a composite core created from one or more selected formations to represent a particular set of one or more subterranean formations. In such event the focus is the impact of the drilling operation on the interface of the various formations recreated within the composite core sample.

The system permits the introduction of a variety of downhole conditions including extreme bore pressure representing the overburden pressure, the static drilling string/bit load, and the dynamic drilling load from the bit, pore pressure representing the fluid load introduced into the core sample, confining pressure around the core sample representing the load on the core sample from the adjacent formation. Additionally, the core sample can be exposed to extreme temperature introduced into the drilling fluids being evaluated and/or by heating or cooling the sample. These downhole conditions can be simulated in a variety of combinations to simulate, for example, a deep hole drilling operation. Such may include, for example, simulating a downhole overburden and drilling loads on the order of 20,000 psi while heating the fluids under evaluation to temperatures on the order of about 400° F.

The system also permits the study of the integrity of the drill bit within the core sample and an accurate measurement of the displacement of the bit within the core sample under such extreme operating conditions. Further, the frictional impact caused by the rotation of the bit can be measured again under extreme operating and drilling conditions. The system can measure not just a compressive load on the sample core caused by these extreme conditions but also fractures, voids, of other geological anomalies created by the various parameters and fluid properties used. These geologically related events including their size and orientations are measured axially and radially by acoustic sensors, electromagnetic sensors and Wheatstone Bridge sensors as described herein.

By evaluating a core sample under these extreme in situ conditions, the immediate impact on the core is demonstrated and the impact specific drilling and treating fluids may have, demonstrated. In addition, the interaction of the fluids and the sample can be studied yielding an in situ comparison between the various fluids being tested and the subterranean formation. Thus, a specific cocktail of fluids may be developed for the drilling and treatment of a particular formation thousands of feet below the earth's surface.

Referring to FIGS. 1 and 2, system 100 illustrates the drilling simulation system of the present invention. System 100 comprises a series of components which will be briefly described below and then followed with a more thorough discussion of each.

System 100 comprises a mud tank skid 200 which supports vats 210, 212, and 214. Referring to FIGS. 1 and 2, vats 212/214 store various drilling and treating fluids under investigation on a test core sample. Vat 210 stores waste fluid used to purge the system upon completion of the test. Drilling and treating fluids stored in vats 212 and 214 are in fluid communication through lines 217 and 219 with the next assembly of the system, skid 300. System 100 also includes a progressive cavity pump skid 300. Referring to FIGS. 1 and 2, skid 300 supports progressive cavity pumps 310 and 320. The advantage of using cavity pumps is that it can generate a steady flow without applying any artificial shear forces to the fluid as it pumps.

Pumps 310/320 are in fluid communication with vats 212/214 via lines 217/219 and serve to advance the drilling fluid through system 100 at a selectable rate of about 0-4 gallons per minute. Skid 300 also supports a Coriolis meter 380 in fluid communication with, and downstream of, pumps 310/320. Meter 380 serves to measure the density, volume, rate and mass of the drilling or treating fluid.

System 100 further includes process tank skid 400 and an intensifier pump sub-system. Referring to FIGS. 1 and 2, skid 400 supports a hydraulic fluid reservoir tank 410. Tank 410 is in fluid communication via lines 402, 403, 404 with an intensifier pump sub-system comprising intensifier pumps 420 and 430. Lines 402/403/404 may also include valves 450 for directional control of the hydraulic fluid from reservoir tank 410. Pumps 420 are used to pressure the hydraulic fluid that pressurizes the accumulators 520/530 as discussed below. Pump 430 is used to introduce confining pressure around the core sample as will be described in more detail below. Pumps 420/430 are preferably servo-controlled metered pumps well known to those skilled in the art as further described below.

System 100 also includes an accumulator skid 500 supporting two accumulators 520 and 530 as shown. An accumulator is used to build up pressure and store fluid volume to address sudden increases or decreases in pressure. Referring to FIGS. 1 and 2, accumulators 520/530 are in fluid communication at their upper ends 540 through lines 550 with the drilling fluid leaving the Coriolis meter 380. Such accumulators 520/530 are sometimes known as "flow-through accumulators" as they ensure that pressure and flow is maintained while simultaneously suspending the solids in the fluid during the dynamic flow state.

At their upper cylinder head 555, each accumulator 520/530 is in fluid communication with the intensified hydraulic fluid from intensifier pumps 420 at junction 570. Drilling fluid entering line 550 from meter 380 is re-routed through a hollow portion 512 of piston stem 514. Thus, fluid passes through each piston stem 514 of accumulators 520/530 into the chambers 516 of accumulators 520/530. With the enhanced pressures created by intensifier pumps 420 the fluid passes into the top portion above the piston head within the cylinders thereby compressing the cylinder to the desired high testing pressures, i.e. 20,000 psi. In this manner, each accumulator 520/530 may introduce significant fluid pressure into the drilling fluids which is representative of significant overburden pressures and static and dynamic drilling loads. Each accumulator 520/530 may also serve to avoid sudden increases or decreases in the drilling fluid volume which is helpful. The use of two accumulators 520/530 is preferred because once the stroke of accumulator 520, for example, is complete and retracting for energizing, the other accumulator 530 is used to ensure consistent high pressure and to avoiding sudden increases or decreases in the drilling fluid pressure movement. In this way, the two accumulators 520/530 work in tandem. Once again, balancing the shift from one accumulator 520 to the other one 530 is achieved through a series of valves 580.

System 100 further includes drilling table 600. Referring to FIGS. 1 and 2, table 600 supports a drilling and testing sub-system. Table 600 supports a test structure 610. Supported within structure 610 is a test chamber structure 620 into which the test core sample 630 is placed. Test structure 610 exerts a downward mechanical force through the members 640 of test structure 610 to simulate the overburden force above the core sample, in other words, the weight of the earth (water and rock) above the location of the core sample under evaluation. The pressure of the drilling fluid, set by accumulators 520/530, serves to provide the necessary load needed to overcome the mechanical overburden force and to get the fluid to the location of the core sample in the subject formation under evaluation. In this manner, the overburden pressure is introduced mechanically by the test structure and then the drilling fluid pressure and static/dynamic drilling load are augmented by the accumulators and introduced onto core sample 630 as discussed further below.

Intensifier pump 430 of skid 400 is connected at junction 632 of table 600 to introduce a confining pressure against the core sample 630. This confining pressure represents the pressure of the adjacent formation to more accurately simulate the continuity of the subterranean formation against core sample 630.

System 100 also includes a pore pressure process tank skid 700. Referring to FIGS. 1 and 2, skid 700 supports a hydraulic reservoir 720 in fluid communication with intensifier pumps 740. Pumps 740 are in turn in communication via line 750 with test structure 610 and the interior chamber 624 of test structure 620 in which core sample 630 is located as described in more detail below. Pumps 740 introduce pore pressure onto the core sample 630. In this manner, core sample 630 is subjected to additional pressure representing the pore saturation core sample 630 as a function of the porosity of core sample 630. Thus, as high-pressure drilling fluid enters chamber 620 by means of line 612, core sample 630 is subjected to a number of variable pressure conditions including high-pressure drilling effects, confining pressure, and pore pressure.

System 100 further includes a control flow loop skid 800. Referring to FIGS. 1 and 2, skid 800 supports a flow loop 810 providing for ingress at junctions 820 from the egress of the testing chamber 620. Flow loop skid 800 comprises a loop from line 810 through either line 830 or 840. Each loop provides a filter bank to clean the fluid. Thus, the operator may cycle the fluid through either loop depending on the condition of each filter bank. Valves 860 are opened or closed to effect this transfer in a manner well known to those skilled in the art. Following passing through either filter bank the fluid passes through a second Coriolis meter 861. As discussed below, the reading from Coriolis meter 861 is compared with the initial reading from Coriolis meter 380. Using mass balance equations on the results of the two Coriolis meters 380/861, the difference in density, mass, and flow rate is reflected. These results reflect the impact the various pressures and temperatures have had on the drilling fluid and core sample. Thus, an operator will know if a particular fluid will achieve the intended results in a particular subterranean formation from which the core sample was extracted.

To heat the drilling fluid to temperatures of about 400° F., one or more heaters may be used at various locations within system 100 such as between skids 200 and 300, between skids 400 and 500, and between skids 500 and 600. Such fluid heaters may be added to components as well and may be resistance heaters or heat exchangers well known to those skilled in the art.

In addition, chillers may be used to cool the fluid and the core sample to simulate extreme cold temperature in artic conditions, particularly during the start-up conditions of a drilling operation when the drilling fluid may be a temperatures only slightly above freezing, and the rock formation nearer the surface may be below freezing. Such chillers may be located at various locations such as between skids 200 and 300, between skids 400 and 500, and between skids 500 and 600. Such chillers may be Model AD15R-40-A11B, manufactured by PolyScience Company of Niles, Ill., www.polyscience.com.

Furthermore, if the fluid is heated then it may be chilled by chiller 890 to ambient temperature once the test is finished and the fluid is to be purged. Since the fluid may be heated to temperatures of about 400° F., it may be preferable to chill the fluid to be properly and safely handled for disposal.

To provide a more detailed description of each sub-assembly, a discussion of each sub-assembly is provided.
Fluid Sub-System Supported within Skid 200

Referring now to FIGS. 2 and 3A-C, skid 200 comprises a frame 270 fabricated from members 271. Frame 270 is supported on base 272. Wheels 274 may be attached to base 272 for moving skid 200 before piping is connected at adjacent skid modules. Vat 210 is used for holding waste fluids and vats 212/214 are typically used for holding the drilling and treating fluids to be evaluated by system 100. In this manner vats 210/212/214 are supported by frame 270 on skid 200.

Fluids are removed from vats 212 and 214 through lines 217 and 219, respectively. In this manner using valves 230, the fluids under investigation, which may be drilling fluid or various treating fluids, are selectively introduced into system 100 from lines 217/219 into line 330 of the flow system supported on the progressive cavity pump skid 300.

Frame 270 also supports injector pumps 260 and 261 which are located on lines 218 and 219, respectively. Lines 218/220 begin at the top of corresponding vats 121/214. Following testing, pumps 260/261 are used to purge the fluid from the entire system 100. Pumps 260 and 261 are commercially available as, for example, model number P1/PP-PPP from the Wilden Pump and Engineering Company, LLC of Grand Terrace, Calif., www.wildenstore.psddover.com.

Vat 210 is used to store waste fluid following testing prior to purging and cleaning the entire system. Vat 210 is drained by opening line 216 to pumps 260 and 261. In this manner, pumps 260/261 purge all the fluid though ports A into waste disposal containers.

Progressive Cavity Pump Sub-System Supported within Skid 300

Figure 4A:
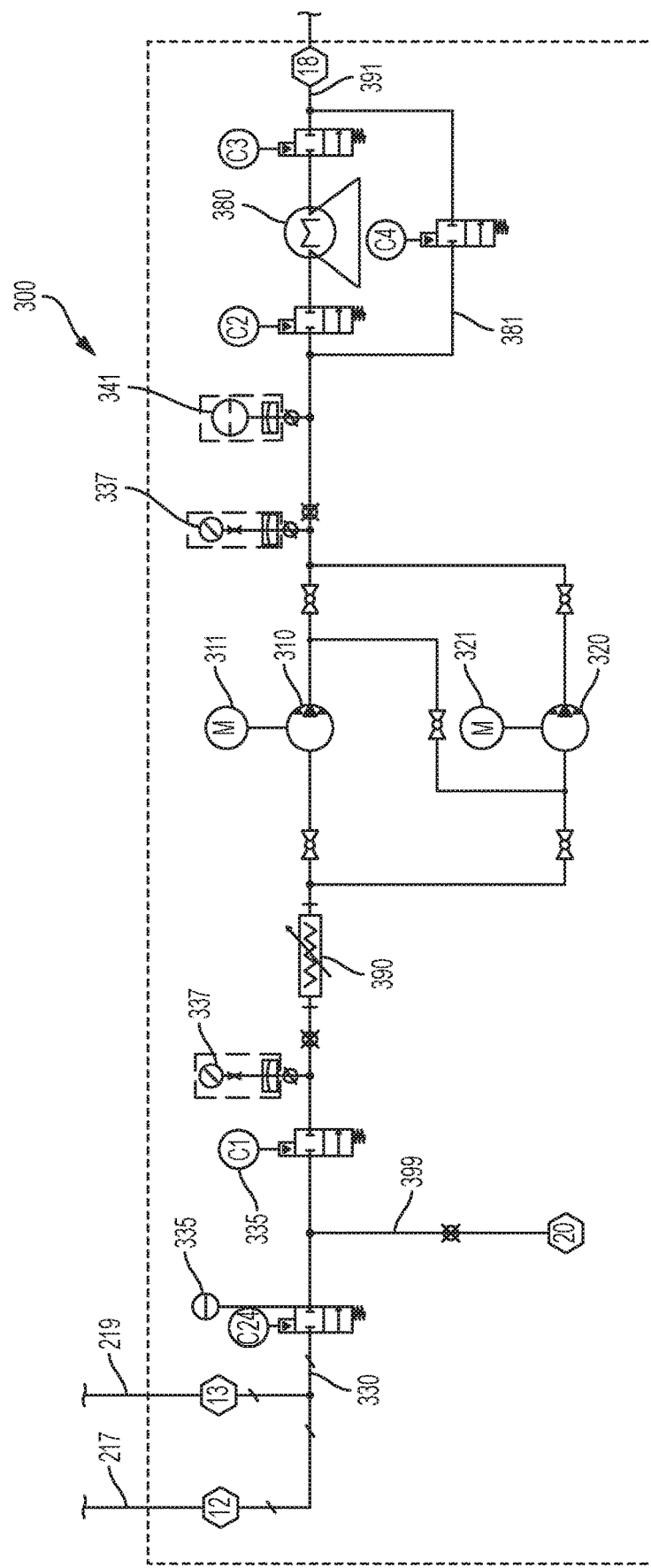
FIG. 4A is a schematic of the progressive cavity pump sub-system of the present invention.
Figure 4B:
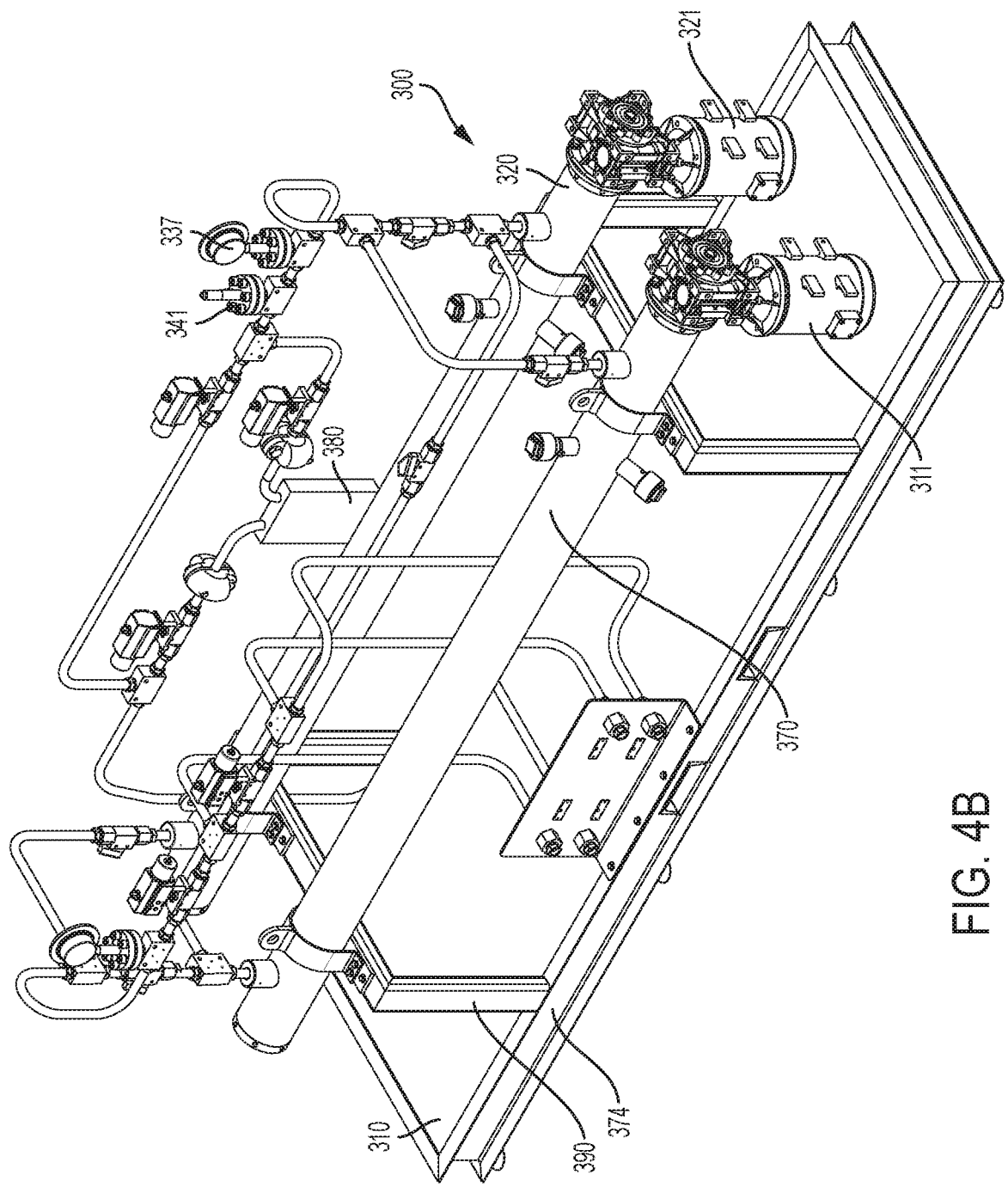
FIG. 4B is a perspective view of the progressive cavity pump sub-system of the present invention.

Referring now to FIGS. 2 and 4A-B, skid 300 supports the progressive cavity pumps sub-system used to provide circulation for the fluid under testing. Skid 300 comprises a support frame 370 having a base 374 and frame 390 to support progressive cavity pumps 310/320 and their corresponding motors 311 and 321.

Fluid to be evaluated enters the system through line 330 passes a series of actuator valves 335, pressure gauge 337, and thermocouple 339. The fluid is advanced forward by pumps 310 or 320 driven by corresponding motors 311/321. Progressive cavity pumps are used since they provide a very accurate volume of pumped fluid without risk of shearing the fluids. Such is important in measuring the results generated from system 100. Cavity pumps operate on an Archimedean screw principle and are well known to those skilled in the art for their accuracy and reliability. Pumps 310/320 are commercially available as, for example, model number 895-4000 from National Oilfield Varco of Fort Worth, Tex., www.nov.com. In the operation of system 100 pumps 310/320 would typically operate in the range of about 0 gallons per minute to about 4 gallons per minute, more preferably in the range of about 2 gallons per minute to about 3 gallons per minute, and most preferable in the range of about 2.5 gallons per minute to about 3 gallons per minute.

As the fluid leaves either pump 310 or 320, it again passes through a pressure gauge 337 and a pressure transducer 341. At that point, the fluid would either pass through a Coriolis meter 380 or alternatively bypassed the meter through line 381. Most often, the fluid would pass through meter 380 to collect the initial readings of the fluids density, velocity, mass, rate, etc. which will be used subsequently to compare with the same types of measurements from a second Coriolis meter after the fluid has been evaluated in test structure 610. Coriolis meter 380 are commercially available as, for example, model number RHM series from Rheonik Messtechnik GmbH of Odelzhausen, Germany, www.rheonik.com.

The fluid would then leave the progressive cavity pump skid 300 along line 391 and advance into the accumulator sub-system supported by skid 500 into the later and serve the accumulator skid 500.

The pressure transducers, pressure gauges, pneumatic valves, and thermocouples as mentioned throughout this specification are well known to those skilled in the art.

Pressure transducers 341 are commercially available as, for example, model number XSEL from WIKA USA of Pasadena, Tex., www.wika.us.

Pressure gauges 337 are commercially available as, for example, model number 23x.34-4.5 from WIKA USA of Pasadena, Tex., www.wika.us.

Pneumatic values 335 are commercially available as, for example, model number 113466 from Rotork PLC of Bath, UK. www.retork.com.

Thermocouples 668 are commercially available as, for example, model number Type K from Omega of Norfolk, Conn., www.omega.com.

Intensifier Pump Sub-System Supported within Skid 400

Figure 5:
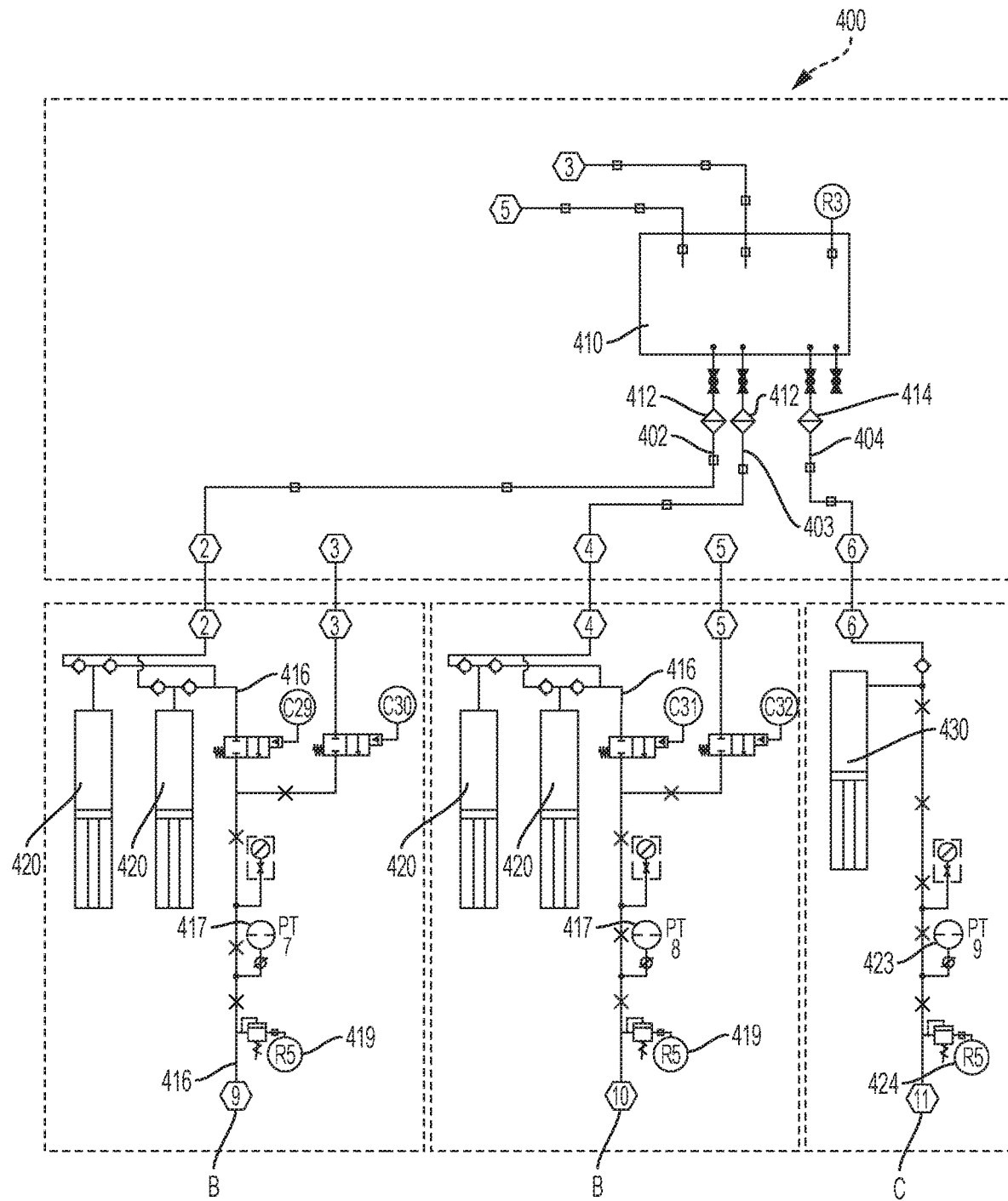
FIG. 5 is a schematic of the intensifier pump sub-system of the present invention.

Referring now to FIGS. 2 and 5, the intensifier pump sub-system is shown. Process tank skid 400 supports a sealed hydraulic reservoir tank 410. Lines 402/403/404 are in fluid communication with tank 410. Hydraulic fluid is allowed to pass through selected valves 412 and filters 414. The hydraulic fluid from lines 402/403 then passes to intensifier pumps 420. Intensifier pumps, well known in the art, serve to increase the hydraulic fluid pressure as needed. Pumps 420/430, which are servo-controlled, compress the hydraulic fluid thereby increasing hydraulic pressure. Pumps 420/430 are commercially available as, for example, from MetaRock Labs of Houston, Tex. www.metarocklab.com.

Increased hydraulic pressure then continues through line 416. The hydraulic pressure is measured at a pressure transducer 417 and a relief valve 419 to exhaust pressure if necessary. The enhanced hydraulic pressure is then exhausted from line 416 at port B. As described below ports B are the entry connection point for the accumulator sub-system, and serve to provide the hydraulic pressure to the accumulator sub-system to assist in creating the overburden load and the static//dynamic drilling loads for the test structure.

A similar operation occurs with respect to pump 430. That is, fluid from line 404 is in fluid communication with intensifier pump 430. Again, pump 430 may be servo-controlled as in the case of pumps 420. The pressure generated by pump 430 is measured by a pressure transducer 423. A relief valve 424 is as available to relieve the pressure of needed, if necessary. The intensified pressure is then available at port C. This pressure at port C will be used to provide the confining pressure onto the test core sample as will be described below. Generally, a higher confining pressure is preferred to evaluate the influence of the combined loads on the sample as discussed below. Typically, such confining pressure may be on the order of 25000 psi.

Accumulator Sub-System Supported within Skid 500

Figure 6A:
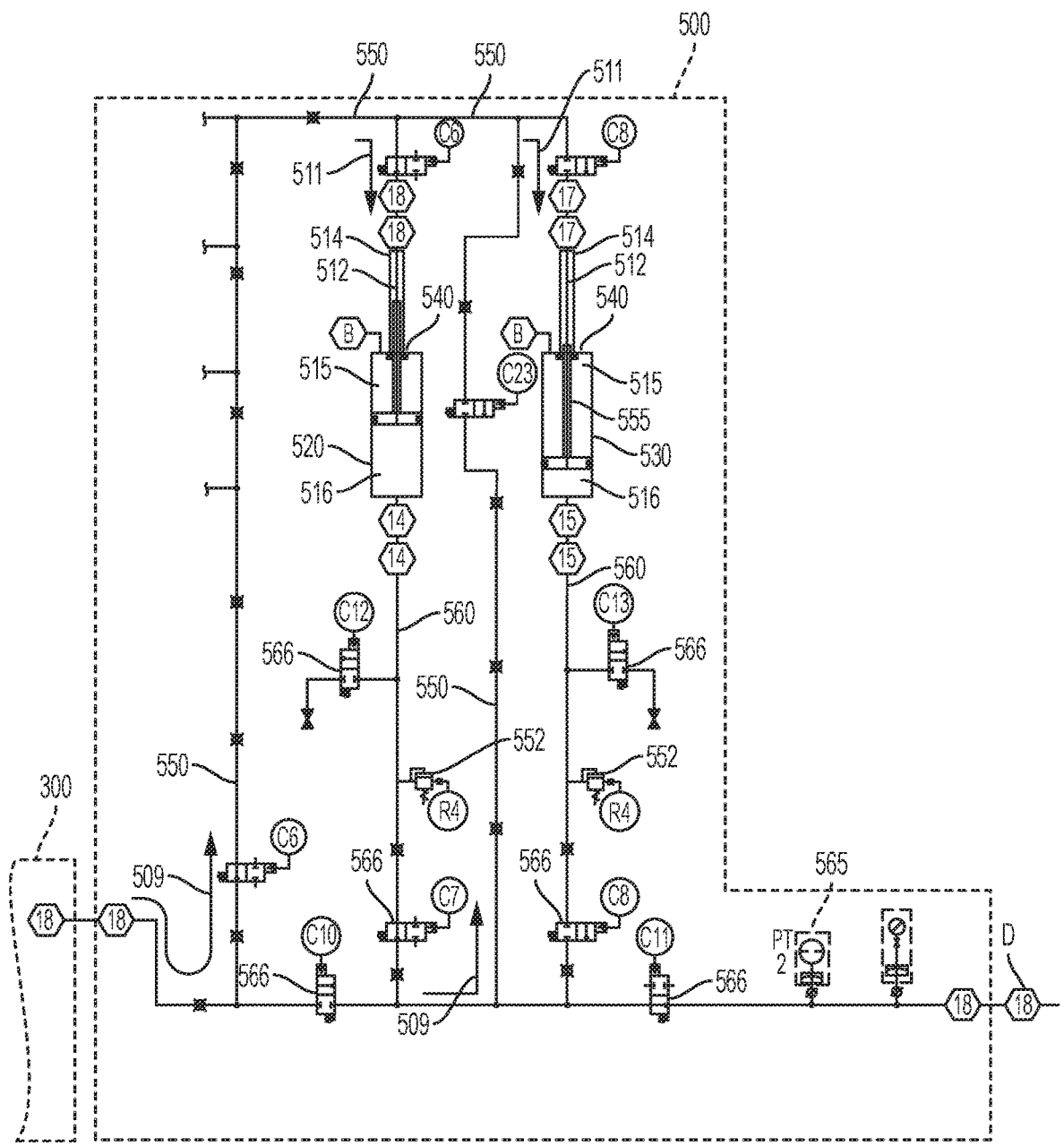
FIG. 6A is a schematic of the accumulator sub-system of the present invention.
Figure 6B:
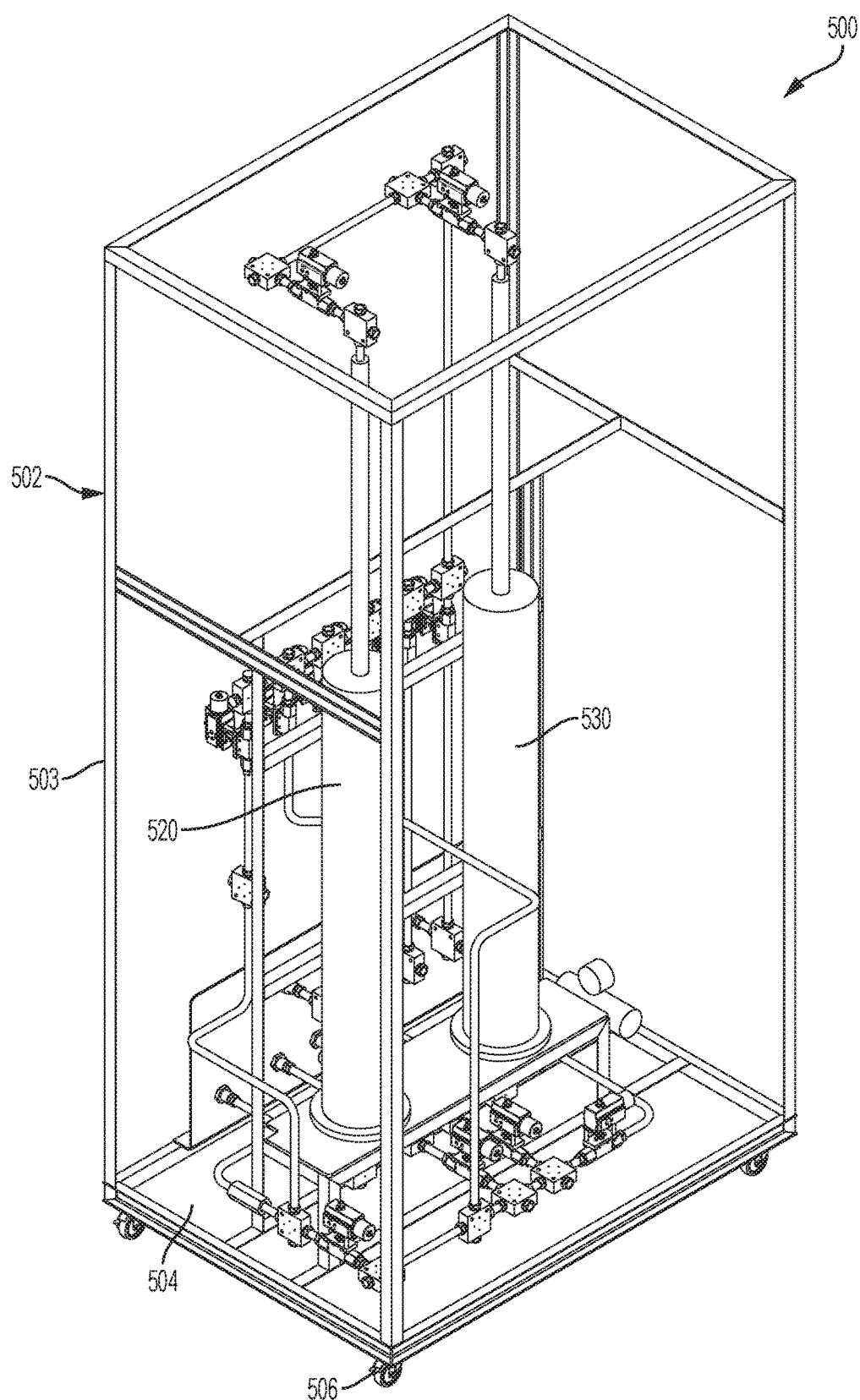
FIG. 6B is a perspective view of the accumulator sub-system of the present invention.

Referring now to FIGS. 2 and 6A-B, accumulator skid 500 comprises a support frame 502 having members 503. Frame 502 is attached to a base 504 which supports the accumulator sub-system. Wheels 506 may be attached to base 504 so that skid 500 may be re-positioned as needed.

The accumulator sub-system comprises preferably at least two accumulators 520 and 530. Each is in fluid communication at their upper ends 540 to lines 550 with the drilling fluid leaving Coriolis meter 380 through line 391 of the progressive cavity pump sub-system supported by skid 300. The drilling or treating fluid under evaluation then flows in the direction of arrows 509 ascending to the top of either accumulator 520 or 530. Each accumulator 520 and 530 operates the same way. The fluid then descends as shown by arrows 511 to the top of an accumulator piston stem 514 of each accumulator 520/530. Each stem 514 includes a hollow portion 512 throughout the length of the stem 514 to provide fluid communication for the drilling fluid as it exits line 550 into the corresponding piston stem 514. The fluid is then in fluid communication with piston chamber 516 of each accumulator 520/530.

The hydraulic pressure generated by intensifier pumps 420 from the intensifier pump sub-system (discussed above) is available at port B as shown in FIG. 5. That port is then connected to corresponding port B of FIG. 6A. This intensified pressure then serves to increase the pressure of the drilling fluid within chambers 516 to the desired loads, i.e. 20,000 psi. In this manner, the intensified hydraulic fluid pressure generated by intensifier pumps 420 raises the fluids under evaluation to the same pressure by means of accumulators 520 and 530. The intensified drilling or treating fluid within chamber chambers 516 then passes through lines 560. Relief valves 552 are installed, if needed. The fluid would then continue past pressure transducer 565 and exit the accumulator sub-system at port D.

In this manner, the fluids under evaluation may either be circulated through lines 550 into the top portion of accumulator 520 or alternatively 530 and permitted to exit lines 560 of either accumulator by the use of various pneumatically operated valves 566 to route the fluid. Two accumulators 520/530 are used in a staggered manner so that one may be active in compressing the fluid to the desired hydraulic pressure introduced at port B while the other is retracting its piston 514 to begin a new cycle when the need arises. Thus, since accumulators 520/540 operate in tandem and flows are regulated by pneumatic valves 566 through corresponding lines 550/560, an operator can maintain a consistent and steady pressurized drilling or treating fluid and can compensate for any sudden increases or decreases of the fluid as the need arises. Accumulators 520/530 are well known in the art and commercially available as, for example, model A50US-Q-0924 of Kocsis Technology of Alsip, Ill. www.kocsistech.com Drilling and Testing Sub-System Supported on Test Table 600

Figure 7A:
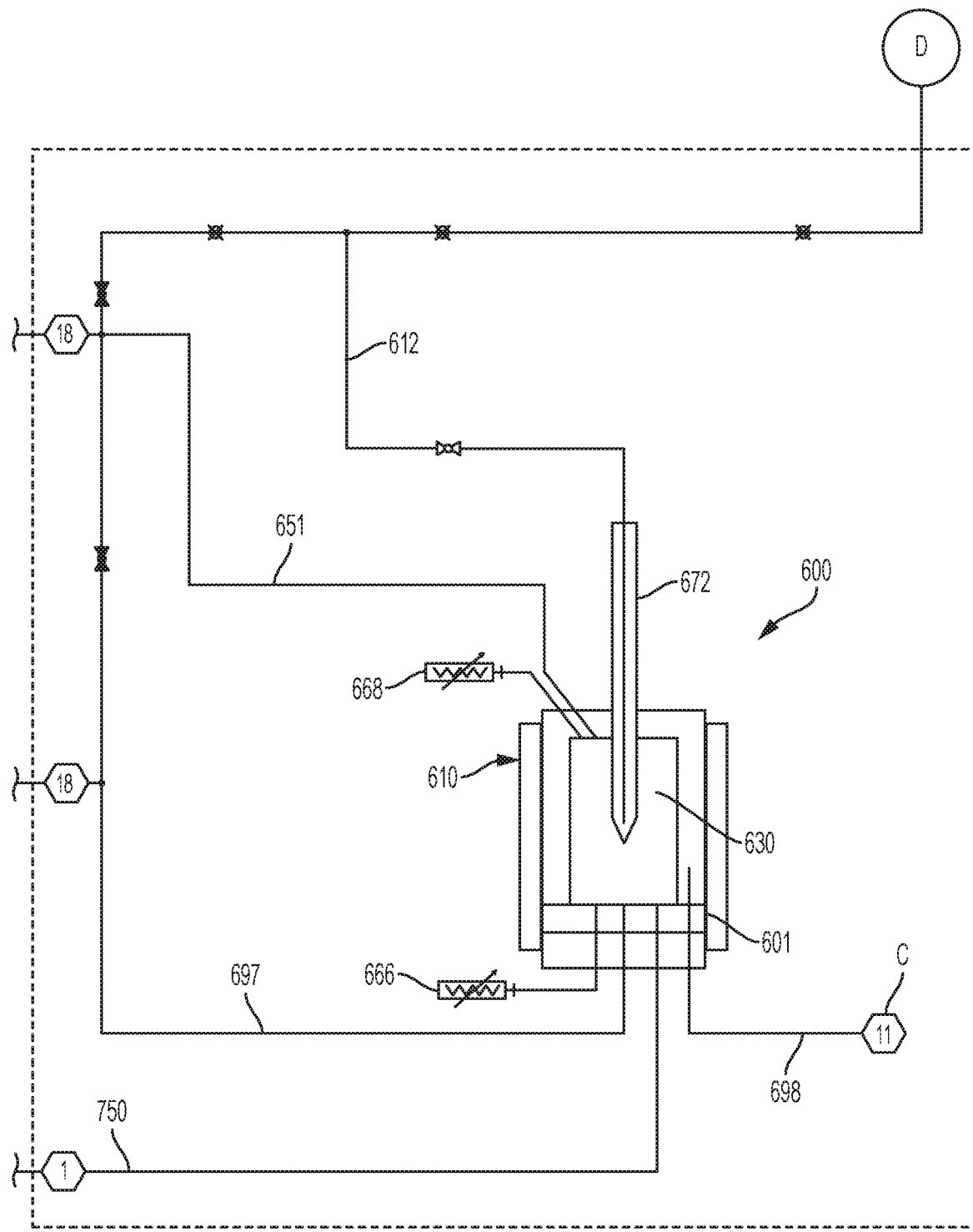
FIG. 7A is a schematic of the drilling and testing sub-system of the present invention.
Figure 7B:
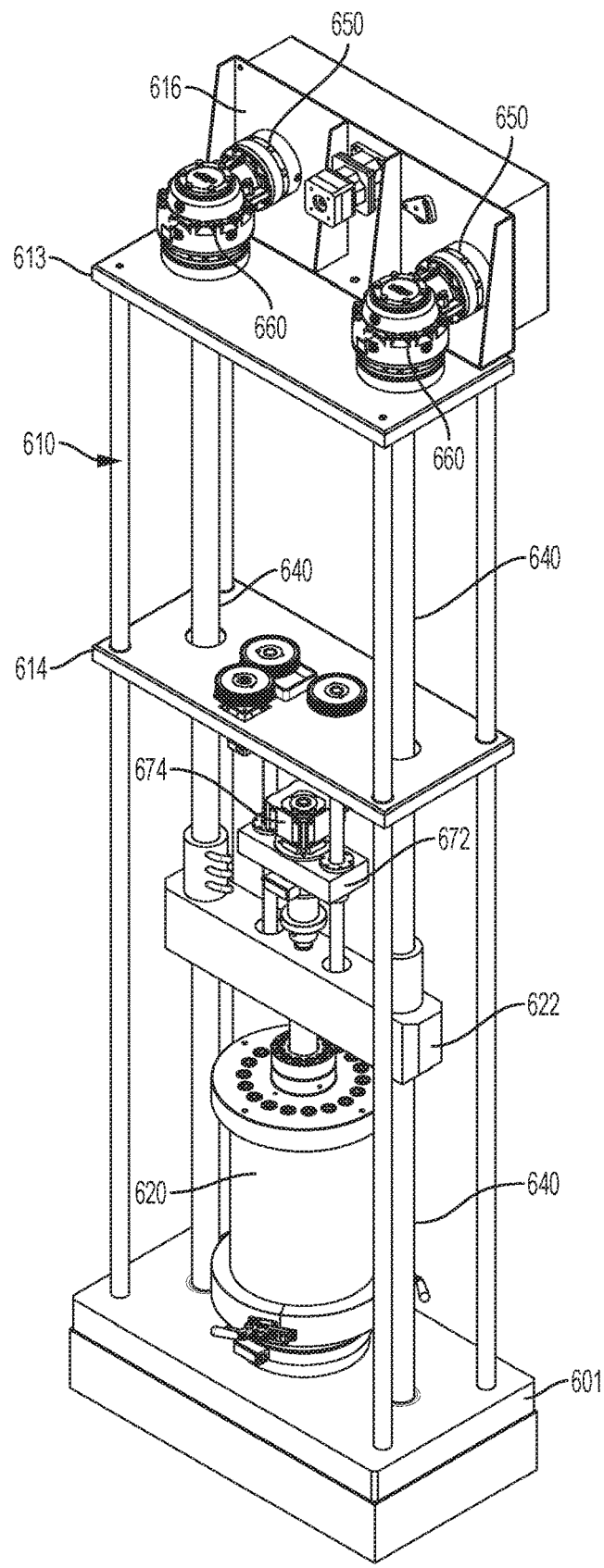
FIG. 7B is a perspective view of the drilling and testing sub-system of the present invention.

Referring now to FIGS. 2 and 7A-E, the fluid under evaluation at port D of the accumulator sub-system (supported on skid 500) discussed above, enters the drilling and testing sub-system supported on table 600 at port D as shown in FIG. 7A.

Figure 7C:
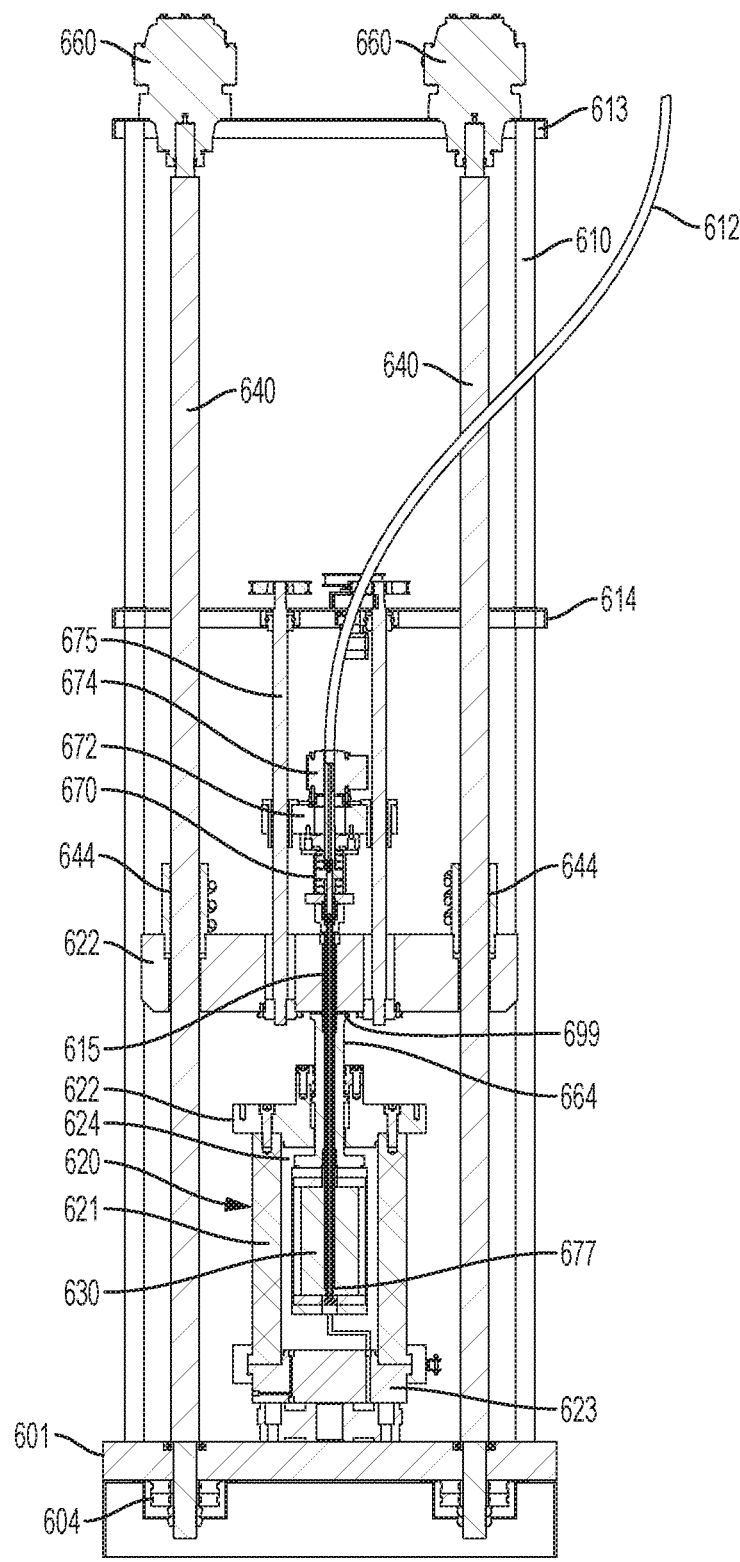
FIG. 7C is a cross-sectional view taken along line 7C-7C of FIG. 7B.
Figure 7D:
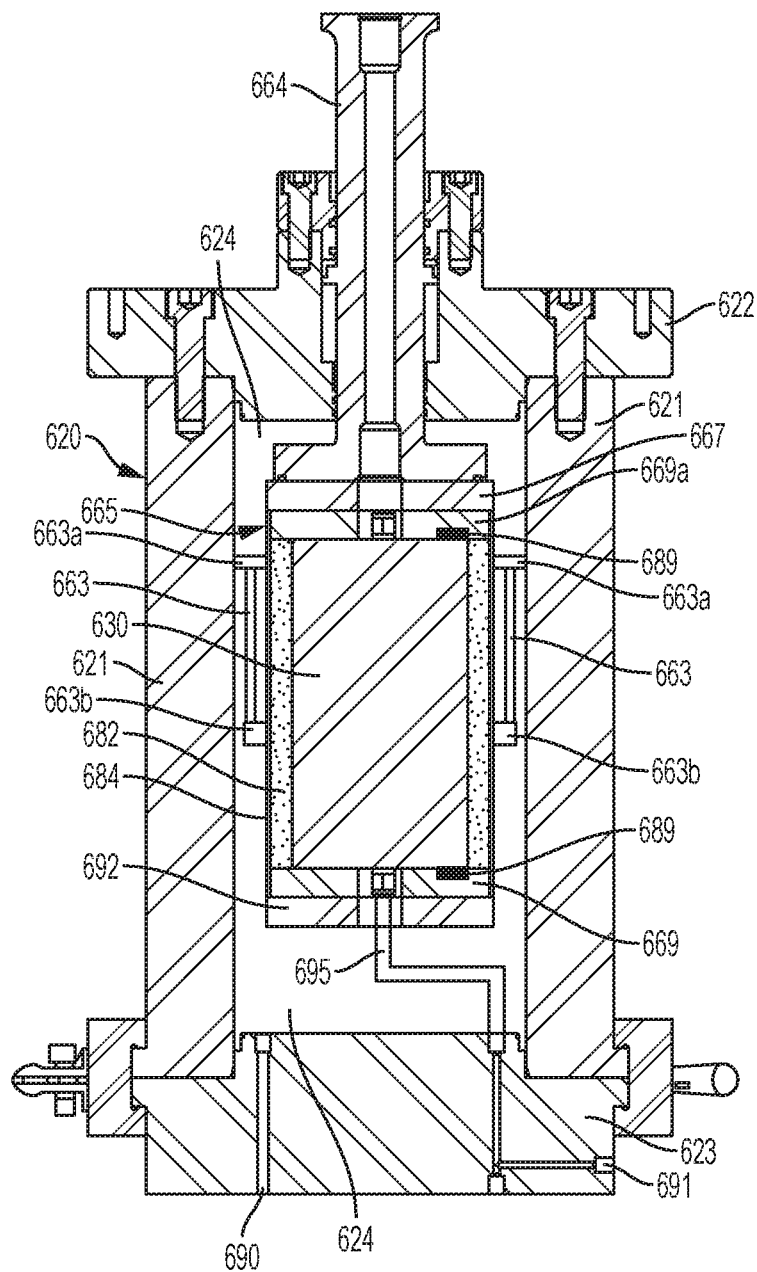
FIG. 7D is an enlarged view test chamber structure of the drilling and testing sub-system of the present invention.

More particularly, referring to FIGS. 7B-E, test structure 610 is attached to base 601 and laterally supported at various levels 613/614. Motors 650 are positioned on level 613 by bracket 616. Each motor 650 engages a gearbox 660 which is rotatably secured to vertical members 640. The lower portion of members 640 are rotatably secured to base 601 by bushings 604 to permit members 640 to rotate but be laterally restrained. Each member 640 includes a threaded section 644 along a portion of its length which is correspondingly threaded to header 622 and can be vertically secured to header 622 before the mechanical load is applied. Header 622 is in turn in contact with the top portion of hollow rod 664 (FIG. 7D).

Test chamber structure 620 is mounted to base 601. Test structure 620 comprises top plate 622, cylindrical body 621, and bottom plate 623, defining an interior chamber 624. Positioned within interior chamber 624 is inner chamber structure 665. Inner chamber structure 665 comprises top plate 667, bottom plate 692, and rubber sleeve 684 which is attached to top plate 667 and bottom plate 692.

In the operation of the testing sub-system core sample 630 is laterally encapsulated with sand 682 and placed within inner chamber structure 665. The inner chamber structure 665 is then supported within interior chamber 624. Rod 664 contacts top plate 667. Motors 650 are started and apply a rotary load to gearboxes 660. This results in a downward load onto members 640 and to header 622. Header 622 then applies the mechanical load onto rod 664 that then applies the load to the core sample 630. Thus, the downward mechanical force applied to members 640, through header 622, onto rod 664 of the inner chamber structure 665 simulates the overburden force above the core sample, in other words, the weight of the earth (water and rock) above the location of the core sample under evaluation.

Referring to FIG. 7C, drill stem 670 comprises a movable head assembly 672 adapted for vertical movement of drill stem 670 into sample 630 along rods 675. Rotary motor 674 is used to separately rotate drill stem 670 and a corresponding bit 677 attached to stem 670 in a manner representative of actual field conditions. Fluid from line 612 (FIG. 7A) is routed through rotary motor 674 and into a hollow elongated section 615 of drill stem 670 and bit 677.

Referring to FIG. 7D, bottom plate 623 includes apertures 690 and 691. Each aperture passes through plate 623 into chamber 624. In this manner, pressures (1) from line 750 of the pore pressure process sub-system (FIG. 1), and (2) at port C from pump 430 of the intensifier pump sub-system (FIG. 5), may be subjected to the core sample 630 as will be further described. LVDT holder 663a secures LVDTs 663 which measure the axial displacement of sample 630 while under testing. Wheatstone Bridge or radial gauges 663b measure radial displacement, which relates to axial displacement, of sample 630 while undergoing testing. LVDT sensors 663 are commercially available as, for example, model number 0234-009 from Trans Tek of Ellington, Conn., www.transtek.com. Acoustical sensors 689 are embedded in bottom plate 669 and top plate 669a. Acoustical sensors 689 transmits a variable sonic wave through sample 630 and thus provides an array image which can look from the top down or from the bottom up. In this manner, acoustical sensors 689 permit triangulation to determine imperfections within sample 630. Acoustical sensors 689 are commercially available as, for example, model number Piezo-Tec Z from Piezo Technology of Seoul, S. Korea, www.piezo-tech.com.

Referring to FIGS. 2 and 7A-D, in the operation of the drilling and testing sub-system, pressurized drilling fluid enters at port D (FIG. 7A) and passes along line 612 to drill stem 670. It then passes through hollow section 615 of drill stem 670, bit 677 (FIG. 7C) into the bore hole being drilled in core sample 630. The fluid arriving at port D has been heated through a series of heaters, discussed below. Thus, the drilling/treating fluid is at the desired temperature for test.

Hydraulic pressure from the pore pressure sub-system supported on skid 700 (discussed below) is introduced through line 750 into aperture 691 at bottom plate 623. Normally, this pore pressure is the same as the overburden pressure, i.e. 20,000 psi. The hydraulic pressure routed through line 691 continues through bottom plate 623 into an aperture nipple 695 located within bottom plate 669 of inner chamber structure 665. In this manner, the pressure generated by intensifier pumps 740 serves to introduce a pressure with in sand 682 that preferably encapsulates core sample 630. Thus, this pressure subjects the core sample to a circumscribing pressure on its pores (influenced by its porosity) represented again by the overburden pressure the core sample would actually experience in situ.

Concurrently, a confining hydraulic pressure from pump 430 of the intensifier pump sub-system which exists at port C of skid 400 (FIG. 5) enters at port C and line 698 (FIG. 7A) and passes through aperture 690 of bottom plate 623. It is then in fluid communication with chamber 624, filling it. This pressure then exerts a lateral load around rubber sleeve 684 of inner chamber structure 665. This pressure thus represents the confining pressure around core sample 630 which is representative of the influence the adjacent formation has on the core sample at the overburden pressure of the selected subterranean formation and may be at a higher pressure, i.e. 25,000 psi.

Figure 7E:
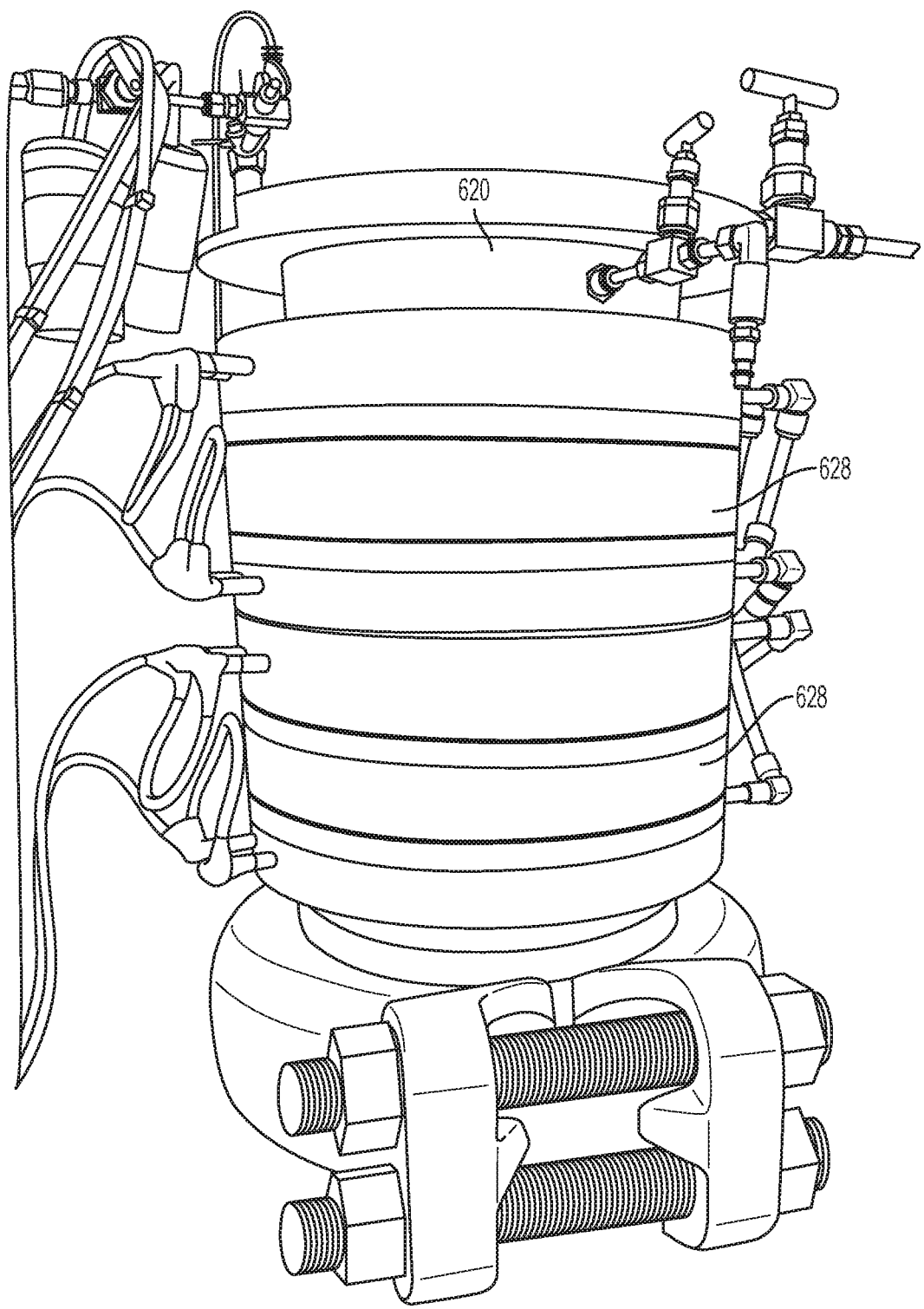
FIG. 7E is another enlarged view of the test chamber showing the temperature jacket of the core sample chamber of the present invention.

In order to subject the core sample to extreme cold temperature, reference is now made to FIG. 7E, the test chamber 620 is circumscribed by a hollow jacket 628 in which a coolant such as R-22 or R-410A is circulated through lines 629 by a coolant compressor (not shown), for example, Mobiltherm® 610 available from ExxonMobil. In this manner the core sample stored within inner test structure 655 may be chilled to temperatures below freezing representing extreme artic temperature. A glycol solution may be used if a heat exchanger is used.

Figure 7F:
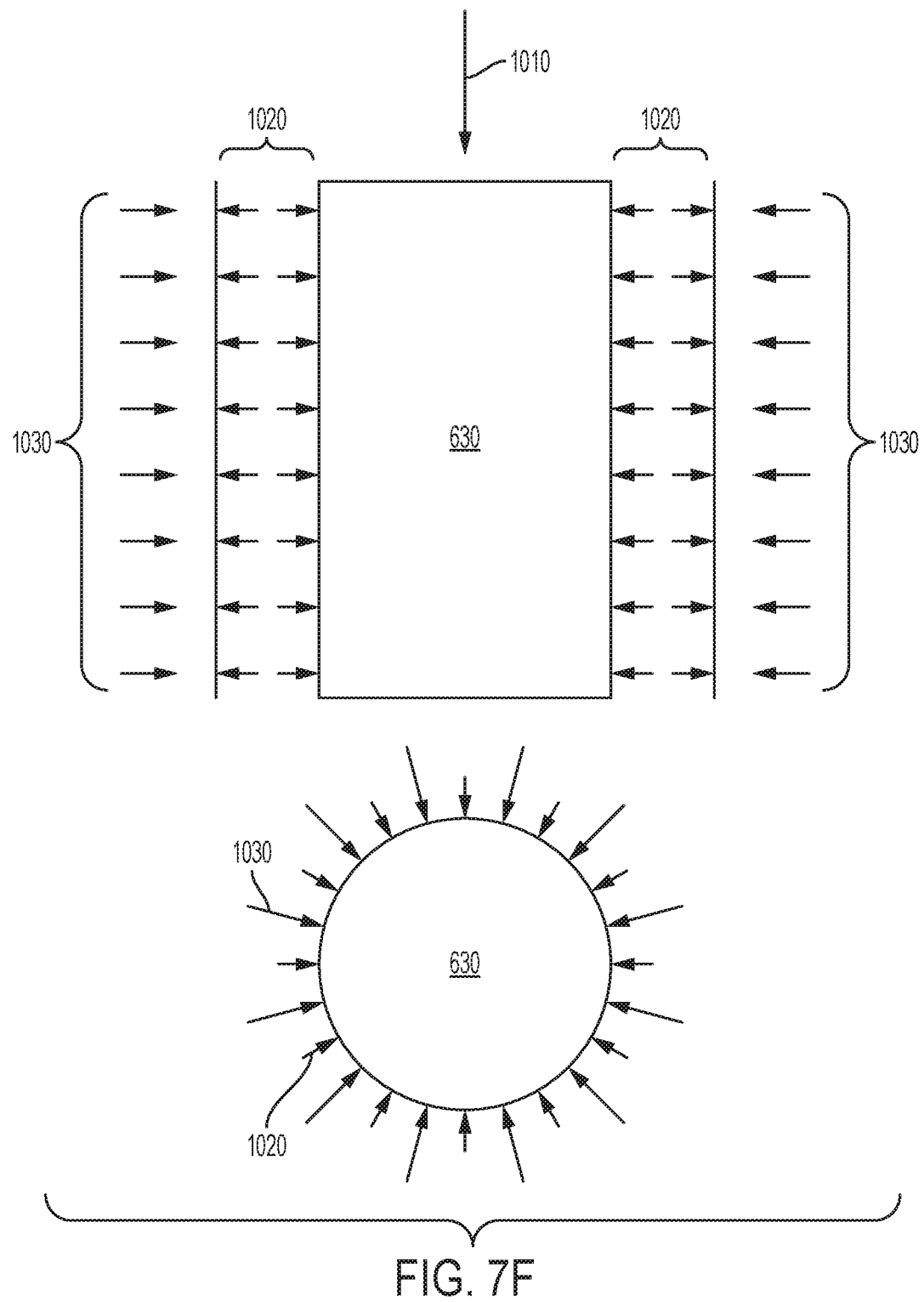
FIG. 7F is an illustrative sketch of the various forces being exerted on the core sample under evaluation in the present invention.

Referring now to FIG. 7F, a schematic of the loads generated by the present invention on test core sample 630 is illustrated. First, there is the mechanical overburden load 1010 generated by motors 650/gearbox 660 onto member 640/headers 622/rod 664 and onto sample 630. This is measured by a load cell 699 (See FIG. 7C) reflecting the load being placed by the test structure on sample 630. Load cell 699 are commercially available as, for example, model LTH500 available from Futek Advanced Sensor Technology, Inc. of Irvine, Calif., www.futek.com.

This mechanical load can be determined by taking the overburden pressure of the subterranean formation and converting it into a load based on the cross-sectional area of the core sample. Then, there is pore pressure 1020 created by the pore pump sub-system on skid 700 which subjects the pores of core sample 630 to the impact of the pore pressure. Pore pressure 1020 is exerted in both lateral directions— against the sample and also against the inner wall of sleeve 684. In this manner, pore fluid under pressure is allowed to migrate within the pores, cracks, and other cavities within the sample and correspondingly influence the behavior of the core sample in an in situ manner to that of the corresponding formation. This will also demonstrate the influence of drilling and treating fluids on the sample as the bit drills into the core. Concurrently, the confining pressure from pump 430 introduces the lateral confining pressure 1030 of the adjacent subterranean formation at the same overburden pressure. In this manner, core sample 630 is subjected to the overburden load and pressures that the representative formation would exert on the test core sample from which it was taken. The confining pressure (i.e., 25000 psi) offers a resistive pressure against the outer surface of sleeve 684 which is larger than the reacting pore pressure (i.e., 20,000 psi).

At this point, core sample 630 is ready to be subjected to the drilling aspect of the test. The drilling/treating fluid and its impact on the core sample 630 is achieved by routing the heated drilling/treating fluid entering at port D through line 612, drill stem 670 and into bit 677. The drill stem is rotated by rotary motor 674 to simulate rotary drilling loads, both static and dynamic, the drilling/treating fluid circulates through bit 677 and into the bore being drilled within the core sample.

In this manner, the combined effect of all the loads described and shown in FIG. 7F and its impact of the drilling load as influenced by the types of drilling/treating fluids being tested on the particular subterranean formation are determined simulating all in situ conditions. For example, an increase in fluid pressure may mean that the sample pack has ruptured and the higher confining pressure has comingled with the lower pressurized drilling or treating fluid.

Drilling/treating fluid is returned from core sample 630 through line 651 (see FIG. 9A) for subsequent analysis in the flow process sub-system supported on skid 800 and disposed or recirculated. The drilling and testing sub-system would include thermocouples 666 and 668 to sense temperature during the testing.

Motors 650 are commercially available as, for example, model number EC2020 from the Brevini USA of Yorktown, Ind., www.brevini.us.

Gearbox 660 are commercially available as, for example, model number B201-5463 from Brevini USA of Yorktown, Ind. www.brevini.us.

Drill bit 677 are commercially available as, for example, model number SC-1A4A from the Scorpion Engineering Company of West Jordan, Utah, www.scorpionengineering.com.

Rotary motor 674 are commercially available as, for example, model number NTM-355-CBNS from the Control Techniques division of the MRO Electric & Supply Company of Cary, N.C., www.mroelectric.com.

Pore Pressure Process Sub-System Supported on Skid 700

Figure 8:
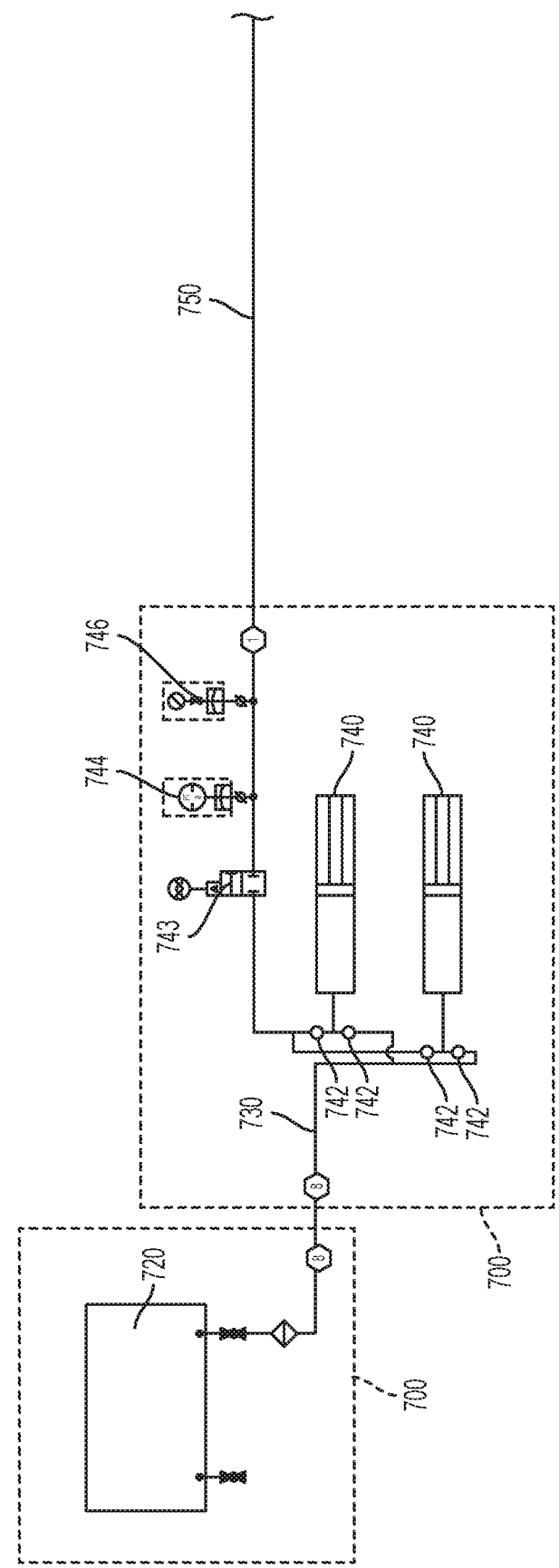
FIG. 8 is a schematic of the pore pressure process sub-system of the present invention.

Referring now to FIGS. 2 and 8, pore pressure process sub-system comprises a skid 700 which supports a reservoir 720. Reservoir 720 is in fluid communication through line 730 with at least one intensifier pump(s) 740. Reservoir 720 stores a fluid to simulate the environment under evaluation. For example, it may be brine, hydraulic fracturing fluid, water or hydrocarbons laced to simulate the oil in the formation under study. A series of one-way check valves 742 are located on lines 730 to ensure the proper flow of the fluid within reservoir 720. Intensifier pumps 740 operate in the same manner as intensifier pumps 420 and 430 discussed above with respect to the intensifier pump sub-system. Pumps 740 are commercially available as, for example, from MetaRock Labs of Houston, Tex. www.metarocklab.com.

As noted above, pumps 740 are servo-controlled and intensify hydraulic pressure by compressing the fluid under evaluation from reservoir 720. The pressurized fluid from reservoir 720 then passes pneumatic actuator valve 743, pressure transducer 744, and pressure gauge 746. The pressurized fluid from reservoir 720 then exits through line 750 and is introduced into aperture 691 at bottom plate 623 of the drilling and testing sub-system described above. In this manner, the pressurized fluid from reservoir 720 is introduced which is representative of the pore pressure load 1020 discussed above with respect to FIG. 7F.

Control Flow Loop Sub-System Supported on Skid 800

Referring now to FIGS. 2 and 9A-C, the control flow loop sub-system comprises skid 800 having a base 805 and members 806 attached to base 805 which served to support the tubing and components of the flow control process sub-system. Wheels (not shown) may be attached to base 805 to provide mobility for skid 800. Plates 808 and 809 support the ingress and egress connections for the flow process control sub-system lines. For example, plate 809 would include the ports E and F and plate 808 would include ports H, I, J.

Figure 9A:
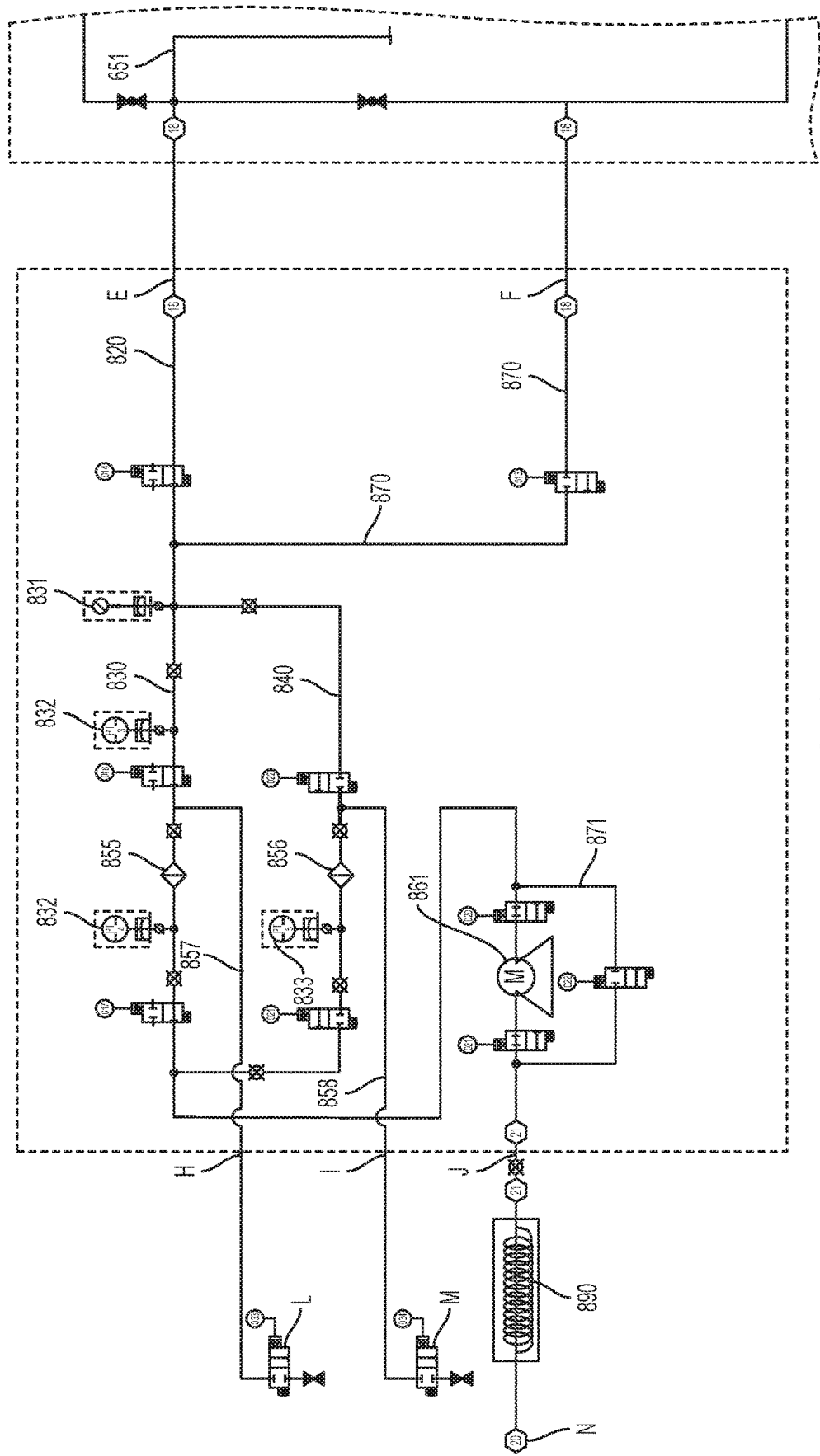
FIG. 9A is a schematic of the control flow loop sub-system of the present invention.
Figure 9B:
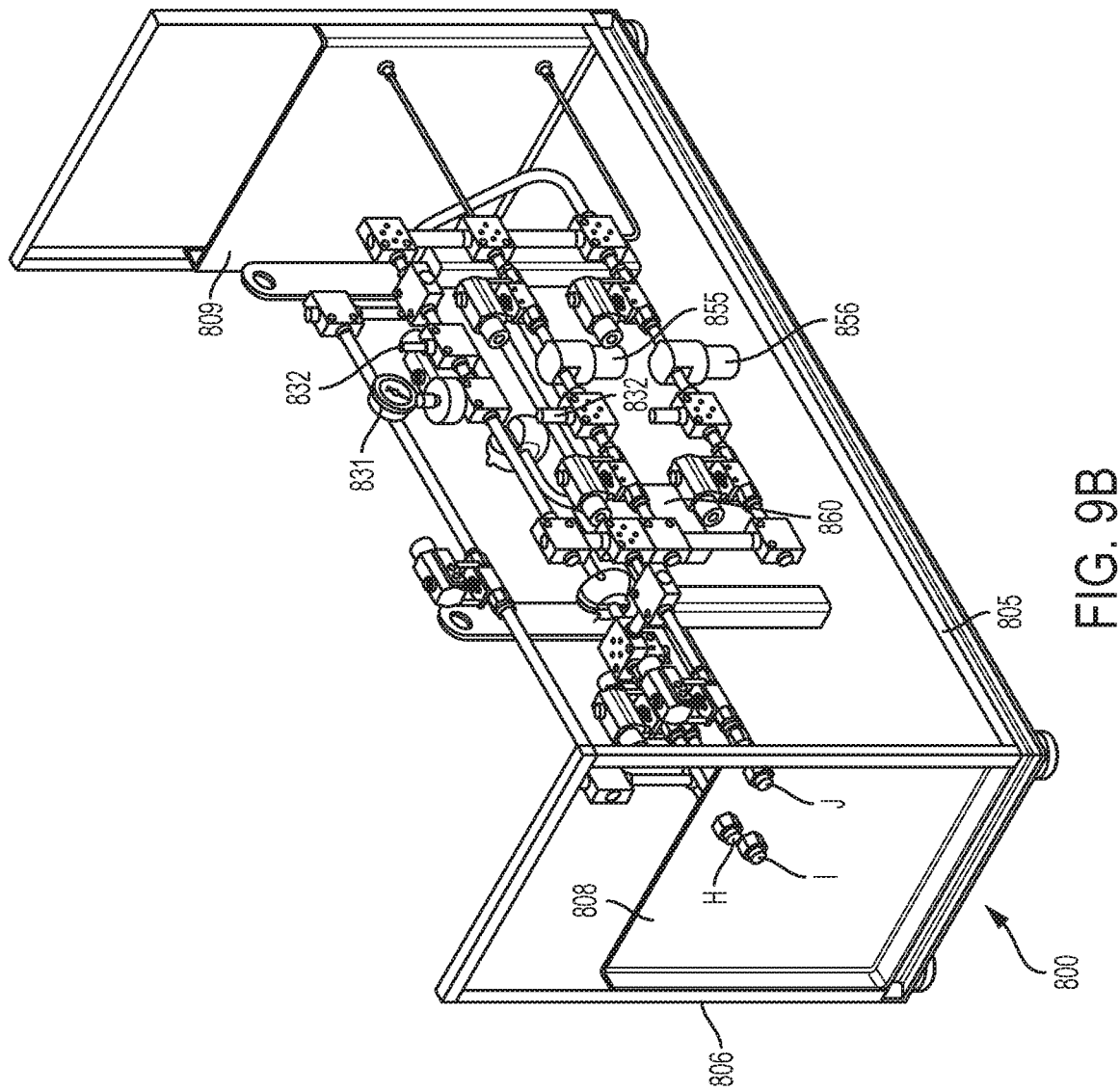
FIG. 9B is a perspective view of the control flow loop sub-system of the present invention.
Figure 9C:
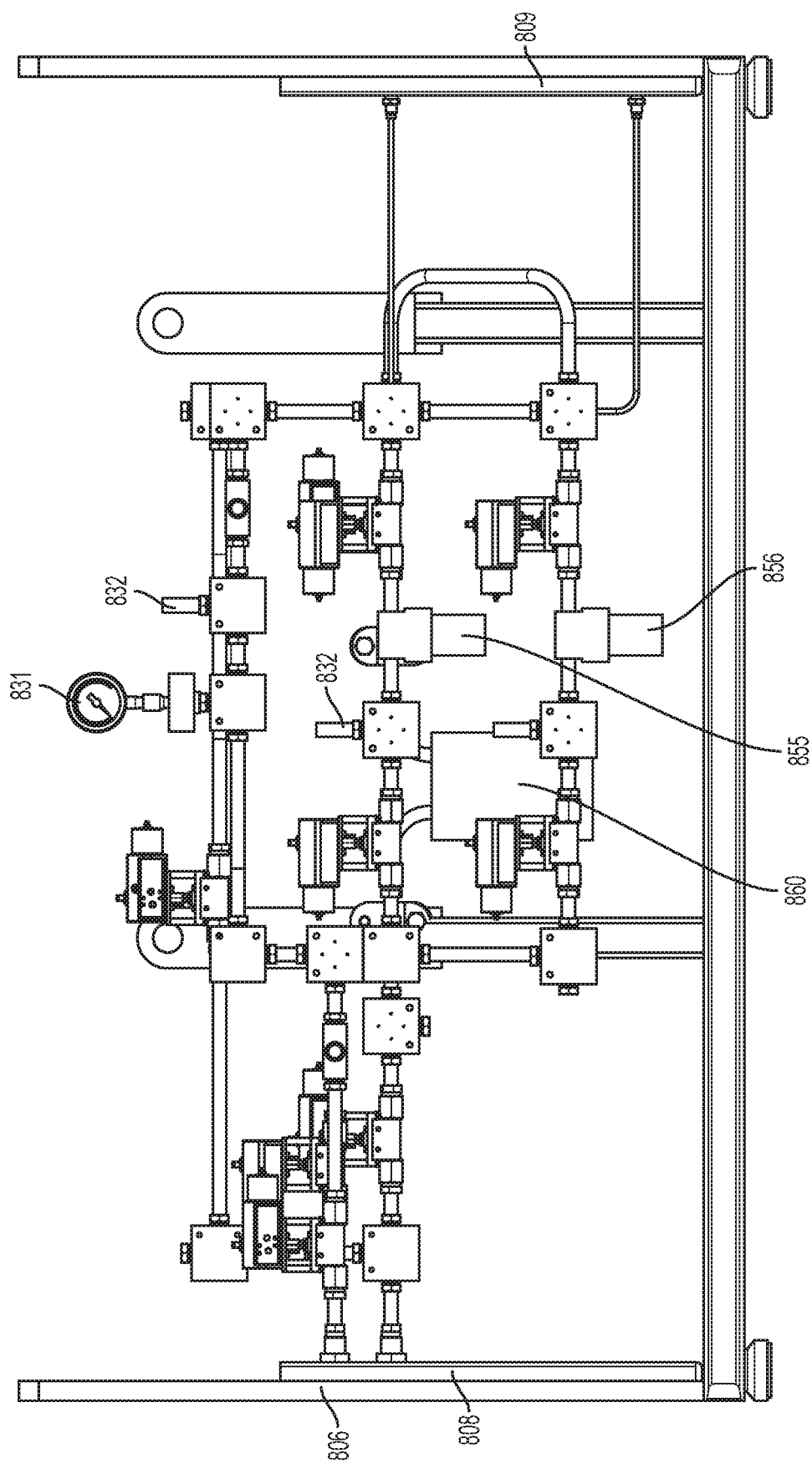
FIG. 9C is an elevation view of the control flow loop sub-system of the present invention.

The lines shown in FIG. 9A provide a sub-system for routing the drilling/treating fluid exiting the drilling and testing sub-system at line 651 through a preselected filter bank and a second Coriolis meter 861 for fluid measurements. The fluid leaving at port J is then passed through chiller 890, or other heat exchanger, to lower the temperature of the fluid and make it safer for proper disposal.

More particularly, drilling/treating fluid leaving the drilling and testing sub-system through line 651 passes into line 820. The fluid may then be circulated through either fluid blank 855 or 856. Alternatively, the fluid may be rerouted through line 870 and recirculated back into the drilling and testing structure through line 697 (FIG. 2).

In operation, the circulating drilling/treating fluid returning from the drilling and testing sub-system passes through line 820 and goes either through line 830 or 840 to either filter bank 855 or 856, respectively. Pressure gauge 831 and pressure transducers 832/833 are positioned along these lines to measure pressure and transmit the results. In this manner, the operator may select either filter bank 855 or 856 depending on the condition of the filter bank at the time of operation. Filter banks 855/856 are commercially available as, for example, model number P8614-V100WE from Hatfield and Company of Rockwall, Tex. www.hatfieldandcompany.com. The sub-system includes sample line 857/port L or line 858/port M ports to draw a sample of the drilling fluid prior to going through either filter bank 855/856.

Once the fluid passes through either filter bank 855 or 856, it is allowed to pass through Coriolis meter 861. As noted before, meter 861 serves to measure the density, volume, rate and mass of the drilling/treating fluid after being subjected to significant downhole in situ pressures and temperatures on the test core sample in the drilling and testing sub-system. The results from the first meter 380 are then compared with the results of the second Coriolis meter 681 to generate in situ results reflecting real time analysis and accurately simulated overburden loads, and static and dynamic drilling loads. Such results provide the operator with the impact of the particular drilling/treating fluid on the core sample to achieve particular results in the drilling operation on the specific formation in question. If an election is made to bypass Coriolis meter 680, line 871 is available. The fluid passes through Port J and through chiller 890 and is returned at port N of FIG. 4A of the progressive cavity pump skid sub-system for recirculation or disposal.

Tubing

The use of the term "line" to describe the piping within the various sub-systems above should not be interpreted in the limiting manner Such lines also may be referred to as tubing or piping. All such terms are substantially equivalent and well known to those skilled in the art in the fabrication of the lines or tubing. Obviously, billet material may be used with holes or cavities drilled in the material to effectively represent passageways instead of tubing.

The selection of the particular size and material used to fabricate the lines or tubing varies depending typically on the maximum anticipated working pressure. For the simulated downhole overburden pressure of 20,000 psi, a working pressure of 21,000 psi is usually selected to include a factor of safety. In such event the size tubing or lines as disclosed herein for the various sub-systems would typical be type 316 stainless steel tubing in the following sizes: ¼" $\phi \times 0.070$"; ⅜" $\phi \times 0.086$"; and 1" $\phi \times 0.219$". In the case of the confining pressure skid 400 the tubing and other piping would be designed for a higher pressure of 25000 psi. Thus, the wall thicknesses would be increased accordingly, well known to those skilled in the art.

Temperatures and Pressures

Furthermore, if the fluid is heated then it may be chilled by chiller 890, or other heat exchanger, to ambient temperature once the test is finished and the fluid is to be purged. Since the fluid may be heated to temperatures of about 400° F., it is useful to cool it so that it may be properly and safely handled for disposal.

Referring to FIG. 2, various heaters are shown to elevate and maintain the drilling/treating fluid to the desired testing temperature. As the system must be capable of accommodating temperatures in excess of 400° F., a series of heaters is preferable to heat the drilling/treating fluid as it circulates through the various sub-systems before it arrives at the drilling and testing sub-system. To achieve such, heaters 2001 are preferably positioned on lines 217 and 219 between the fluid sub-system and the progressive cavity pumps sub-system. Heater 2003 may be positioned on line 391 between the progressive cavity pump sub-system and accumulator sub-system. Heater 2005 may be positioned between the corresponding port D between the accumulator sub-system, and the drilling and testing sub-system. Multiple heater may be used at each of the locations and one of more heaters may not be needed at each of these locations depending on the temperature demands expected. These heaters are preferably radiant heaters commercially available as, for example, model number WJS523266, from Valin Company of San Jose, Calif., www.valin.com. Alternatively, other suitable heaters may be used such as heat exchangers, and such may be mounted to individual components as discussed herein.

As noted above, the present invention is adapted to simulate significant overburden loads, for example, loads generated as a result of 20,000 psi pressure at the subterranean formation. As mentioned, the actual load is determined by multiplying the pressure (i.e., 20,000 psi by the cross-sectional area of the test core sample 630). However, as the final pressure selected is a function of the location of the subterranean formation, the pressure may be more or less.

In view of the teachings of the present invention, a drilling simulation testing system may be provided to accommodate significantly higher pressures by selecting other materials and sizes to accommodate more pressure. For example, the tubing discussed above may be modified in material type and sizes to accommodate higher pressures.

The selection of the number and sizes of heaters is a function of the anticipated testing temperatures and the flow rate of the drilling/treating fluid controlled by the progressive cavity pumps 310/320. The operating temperature range should be between about 300° F. and about 450° F. The preferable temperature range is between about 350° F. and about 425° F. The more preferred temperatures for most testing applications is about 400° F. To achieve these high temperature ranges with a flow rate between about 3 gallons per minute and about 4 gallons per minute by pumps 310/320, six of the types heaters mentioned above may be required. In such event heaters 2001/2003/2005 may comprise a pair of heaters at each such locations or even mounted on components as discussed herein.

In addition, chillers or other heat exchanges may be used to cool the fluid and the core sample to simulate extreme cold temperature in artic conditions, particularly during the start-up conditions of a drilling operation when the drilling fluid may be a temperature only slightly above freezing, and the rock formation nearer the surface may be below freezing. Such chillers may be located at various locations such as between skids 200 and 300, between skids 400 and 500, and between skids 500 and 600, or even mounted on components as discussed herein. Such chillers may be Model AD15R-40-A11B, manufactured by the PolyScience Company of Niles, Ill., www.polyscience.com.

Additionally, connections at the joints of the tubing and in-line instruments, such as the pneumatic valves and pressure transducers, may be designed of materials selected to accommodate higher pressures. The selection of the materials for fabricating the tubing and connectors, including connections with valves, gauges and transducers is well known to those skilled in the art and adaptable based on the teachings of the present invention. The present invention is anticipated to provide pressure in the range of between about 5000 psi and about 30000 psi, preferably between about 15,000 psi and about 25,000 psi, and more preferably about 20,000 psi.

Sensors

Particular sensors as discussed above collect the following type of data:

TABLE I

| Sensor | Measurement Type |
| --- | --- |
| Coriolis Meter | Mass flow rate |
| | Volumetric flow rate |
| | Fluid density |
| | Temperature of fluid |
| LVDT | Axial displacement of sample |
| Wheatstone Bridge | Radial strain of sample |
| Thermocouples | System temperature |
| Pressure Transducer | System pressure |
| Load cell | Press load |
| Drill stem motor | RPM, ROP, Friction, Torque |

Their use within the operation of the system are discussed below with respect to FIG. 10.

Operation

In the operation of the present invention, temperature and overburden pressure are first selected for the drilling/treating fluid under evaluation based on the location of the core sample under review. Typically, it is necessary to elevate the temperature and the pressure to the desired level before testing begins. The length of time it will take to do so will vary depending on the pressures and temperatures selected and the attributes of the core sample selected.

The evaluation typically begins with the preparation of sample 630. A core is selected from a particular formation or representative of a particular formation. It may be pre-shaped based on the quality of the drilling core provided or it may be shaped prior to insertion in the chamber 620.

Additionally, the sample 630 may be fractured by drilling sample 630 before or after evaluation. This is achieved by predisposing sample 630 before evaluation to intentionally created flaws, such as minor perforations, grooves, or holes. These artificial flaws will then be exploited during testing to generate differing types of fractures by the application of excessive overburden forces, managed-pressure-drilling techniques, non-uniform lateral stresses, micro-detonations, twisting of the core, or rapid stress cycling of the core. Thus, the present invention enables deliberate fracturing of core sample 630 to simulate and analyze fluid migration behavior through a specific formation.

The particular drilling or treating fluid is then selected and deposited in vats 212 and 214 of the fluid sub-system as discussed above and shown in FIGS. 3A-C. Which vat for which fluid will depend on the particular mixture the operator desires. Air is purged from the lines and the fluid is then released from the vats 212 and/or 214 and passes through lines 217 and 219 and then through heater 2001.

It then enters the progressive cavity pump sub-system discussed above and shown in FIGS. 4A-B. Preferably, pressure gauge 337, and thermocouple 390 are used to acquire an initial pressure and temperature. Cavity pumps 310 and 320 are selected to pump the fluid at a very precise and yet relatively low rate. This rate continues throughout the entire process to ensure consistency and accuracy. The pressure of the fluid is then measured for the computer by pressure transducer and passes through the first Coriolis meter 380. It is at this point that an initial set of particular properties of the fluid such as density, velocity, mass, and rate are measured.

As the fluid leaves meter 380 it is heated by heater 2003 and enters the accumulator sub-system described above and shown in FIGS. 6A-B. The accumulator sub-system has been previously charged by the intensifier pump sub-system as discussed above and shown in FIG. 5. With the pressure selected for the particular formation, the hydraulic pressure is increased by the servo-controlled intensifier pumps 420/430 to the desired level. The hydraulic fluid leaves ports B and C of the intensifier pump sub-system (FIG. 5) and enters and activates the upper piston chamber 515 of accumulators 520/530. This then places the drilling fluid which is descending to the top of the accumulator's pistons through the hollow portion 512 of stem 514 and into the bottom chamber 516 to be pressurized to the same pressure, i.e. 20,000 psi. The fluid is then routed out of the accumulator sub-system and through heater 2005 to further heat the fluid being evaluated, if desirable.

The drilling/treating fluid then enters through line 612 of the drilling and testing sub-system into drill stem 670 to begin the drilling operation as discussed above with respect to FIGS. 7A-E. As the fluid is circulated it exits through line 651 and into control flow loop sub-system as discussed above with respect to FIGS. 9A-C. The returning fluid may be filtered either through filter bank 855 or 856 and a sample taken accordingly, if necessary, at ports L or M. The fluid then passes through Coriolis meter 861 and a second set of readings preferably identical to the type of readings taken from Coriolis meter 360 is measured. In this manner, using mass balance equations as further discussed below, the operational impact on the drilling or treating fluid determined as well as the fluid's impact on the core sample determined.

The fluid leaving Coriolis meter 861 passes through chiller 890 (used to lower the temperature of the fluid for disposal, if necessary at that time), or the fluid is re-circulated through line 697 again through the progressive cavity pump sub-system to re-enter the entire process.

Figure 3A:
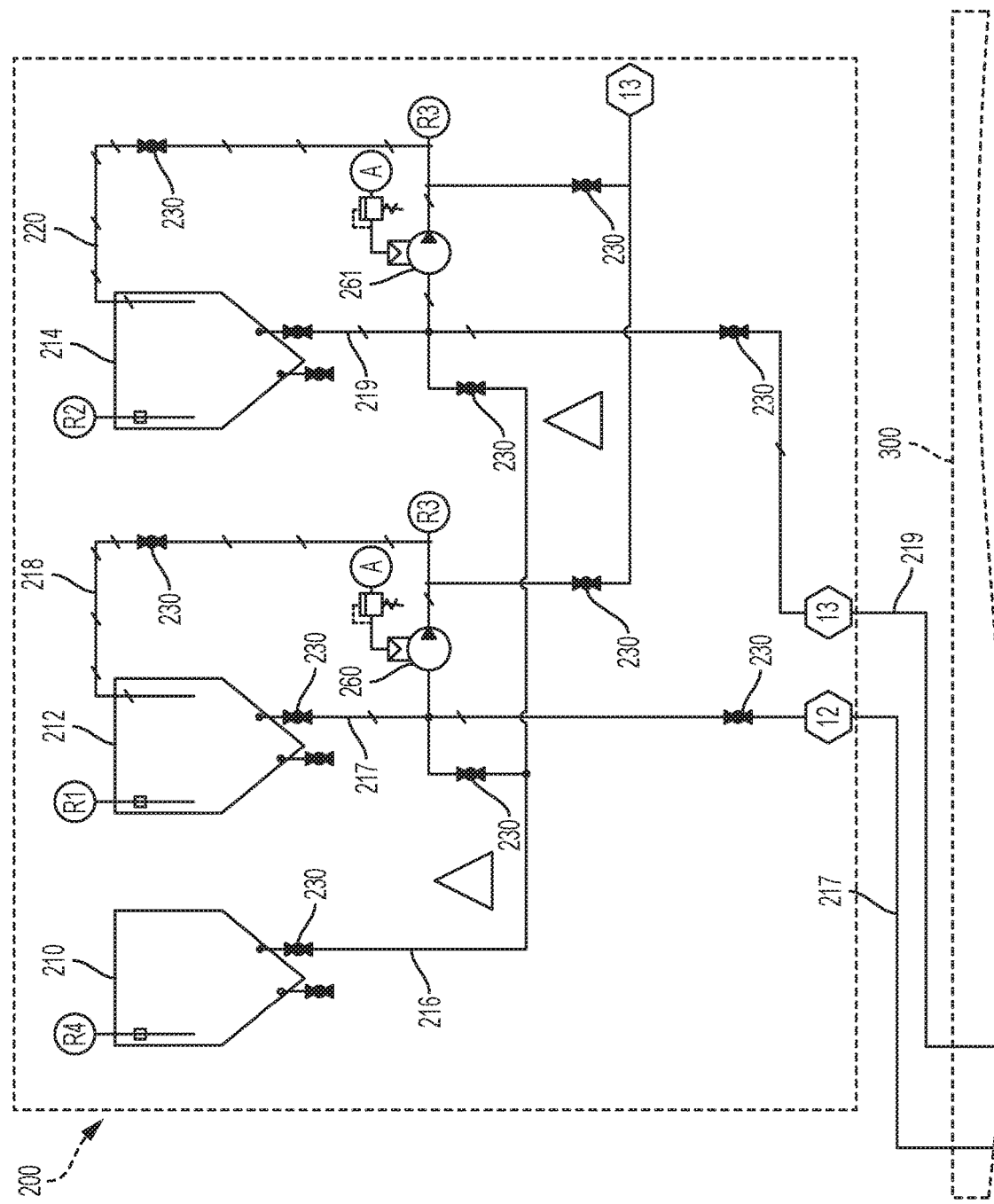
FIG. 3A is a schematic of the fluid sub-system of the present invention.
Figure 3B:
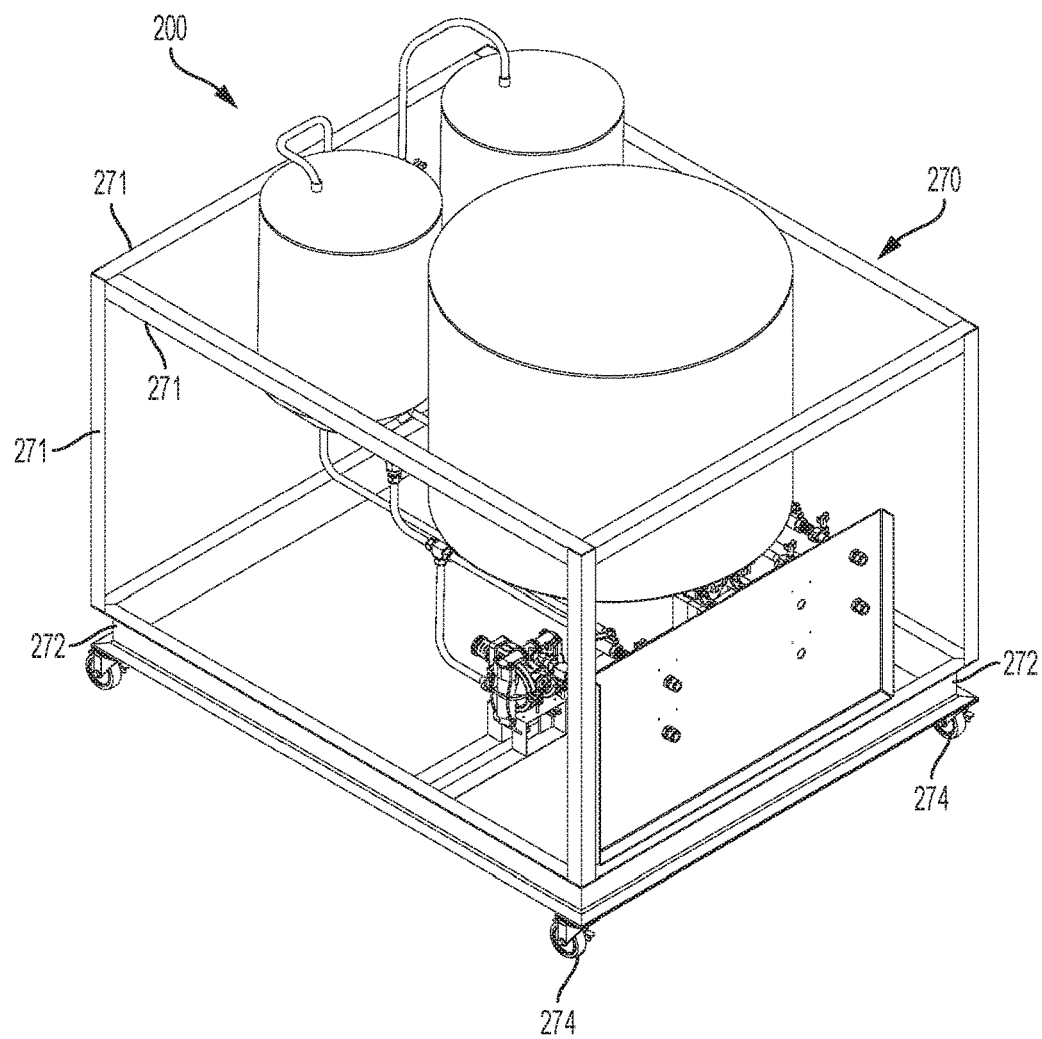
FIG. 3B is a perspective view of the fluid sub-system of the present invention.
Figure 3C:
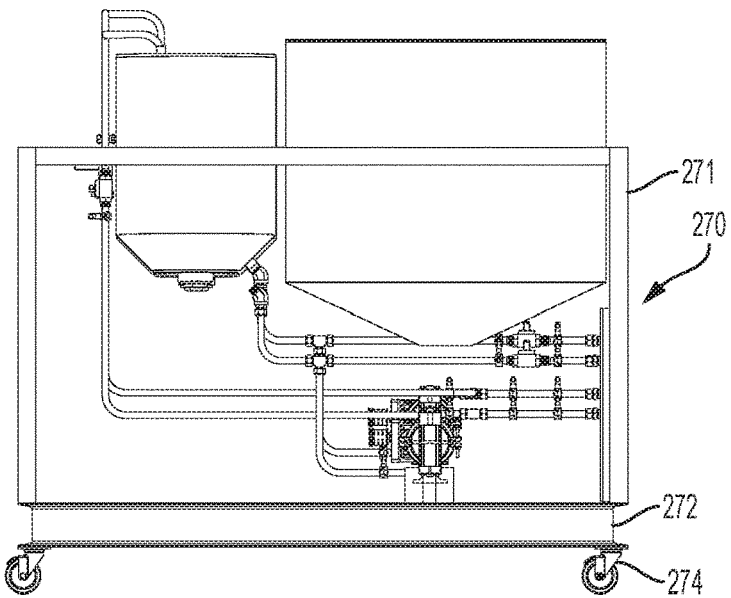
FIG. 3C is an elevation view of the fluid sub-system of the present invention.

Following completion of the testing, system 100 may be purged by activating motors 260/261 of the mud tank sub-system discharging the used fluid at ports A as shown in FIG. 3A for disposal. If necessary, waste water from vat 210 may be used to further purge the entire system as discussed above with respect to FIGS. 3A-C. Instead of waste water clean water, solvent or other fluid may be used.

Flow and mass meters can be used to enhance the ability to collect many complex measurements in real time. Both precision and accuracy become increasingly essential as measurements become hyper-critical indicators of system behaviors. Today's Coriolis meters, such as 380, integrate the aspects of fluid flow as well as mass flow to provide uniquely insightful measurements that are not disruptive to the experiment at hand. The most sophisticated approach is mass balance conclusions.

It is not uncommon for systems to monitor (and control) fluid flowrates through flow meter feedback. Mass balance, however, monitors upstream fluid flowrates for the purpose of baselining behaviors in the sample chamber. Fluids within the boundary of concern are subjected to constant enthalpy through the maintenance of both constant temperature and pressure thereby making fluids of slight compressibility effectively incompressible within the boundary of concern. The incompressibility of these test fluids insures that, barring events in the test chamber or leaks in the system, downstream flowrates mirror upstream flowrates precisely. The same is true for mass flowrates, however, debris and fluid deposited into or removed from the sample chamber will be exposed as it passes through the downstream mass meter. Volumetrically, the flow is generally constant. But from a mass balance perspective the minute fluctuations in mass flow represent powerful indicators of events occurring inside of the testing chamber.

Precise control of both temperature and pressure within the test chamber and surrounding system are crucial in order to apply mass balance principles. Deltas, rather than absolute measures, are used to make critical inferences, but these no longer hold once temperature or pressure are allowed to deviate within the system. Pressure losses exist due to piping realities and the bit nozzle effect, but these are both quantifiable and insignificant to the overall balance.

Referring now to FIGS. 2, 7A-7D, and 9A, generally, at the beginning of an experiment, fluids enter chamber 624 and pass through without any expectation of depositing or removing material with regards to core sample 630. This is accomplished by baselining an experiment with the bypassing flow loop as discussed above with respect to FIG. 9A. This baseline is then validated and confirmed by the downstream mass flowmeter 861. As drilling begins, the debris generated by drilling into core sample 630 begins to be recognizable in the form of elevated mass (or density) of the fluid measured downstream. When coupled with knowledge of the actual displacement of drill bit 677, these values can be compared to expected calculated values and inferences to the quality of the hole being generated can be made; recognizing that core mass is getting steadily converted to heavy debris and then being displaced by fresh fluid.

All inferences that include debris transmission are validated and quantified downstream by the substantial collection of the aforementioned debris in fine mesh filter bank 855 or 856. The filter debris collected should be equal to the amount of mass transfer detected through mass balance provided no pore fluid exchange has taken place. Essentially, any mass of rock drilled out of core sample 630 and any additional debris from core sample 630 released during wellbore deterioration should be accounted for in filter unit 855 or 856, depending on the loop selected.

Once the drilling phase is completed, mass flow is then monitored in order to quantify the amount of fluid being deposited into core sample 630 over time, because under these conditions, the flowrates upstream will not necessary equal the flowrates downstream. The delta here represents the fluid being deposited if the fluid density shows no change. Changing fluid density would be a real-time indicator in a post-drilling situation that the wellbore is deteriorating (releasing debris into the passing fluid), or that a fracturing event has occurred exchanging pore fluids with the drilling fluids. One example of core exchange includes the formation of a membrane (a/k/a filter cake) across the inner surface of the drilled hole. Density decline indicates pore fluid exchange through the core. Density instability and increase would indicate debris transmission from the core. Further, instantaneous events (such as core fracturing) are generally irreversible and would not show correction or stabilization over time.

$$\dot{M} = \rho * Q = \text{fluid density} * \text{volumetric flow rate}$$

$$\Delta\rho = \frac{M_{fluid\ in} - (M_{fluid\ out} + M_{debris})}{V_{fluid\ in}} \text{ (drilled \& post-drilled state)}$$

Also during this post-drilling phase, one can monitor and determine other event-related phenomena that is more subtle in nature using a mass balance approach. These events could take the form of wellbore strengthening activities or lost-circulation recovery. Using mass balancing, one could monitor these impacts in real-time by measuring the depositing material and fluid losses through changes seen in the downstream fluid properties or compositions.

Figure 10:
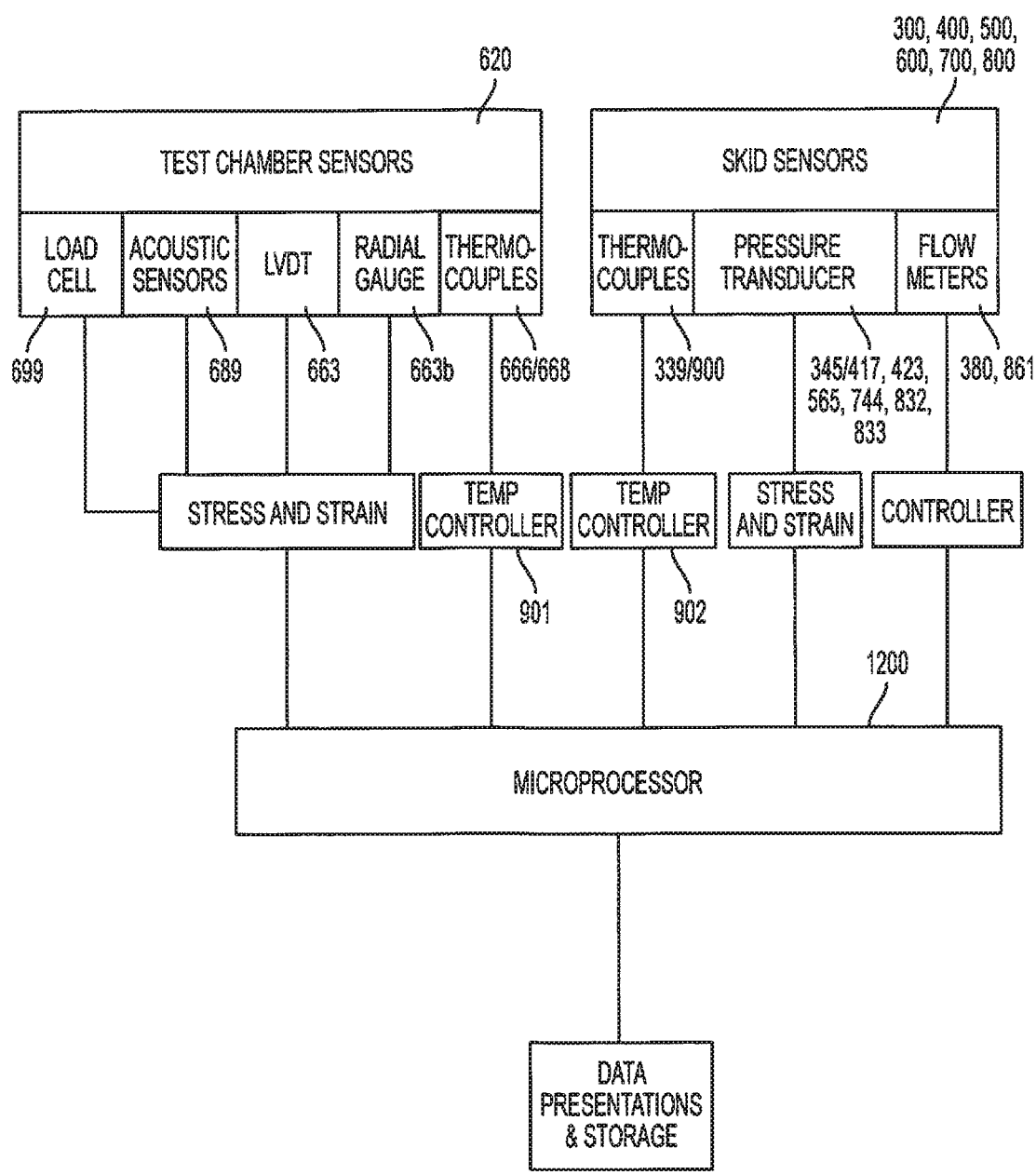
FIG. 10 is a flowchart of the processing of data in the present invention.

Referring now to FIG. 10, the interrelationship of the various sensors will be described within the operation of the present invention. Sensors as discussed above may be categorized into two groups: those used within the test chamber 620 and those found on the various skids 300, 400, 500, 600, 700, and 800.

Referring still to FIG. 10, within chamber 620, there are principally five sensors recording various data. Load cell 699 measures stress and strain, acoustical sensors 689 measure variable acoustical waves, Wheatstone Bridge or radial gauge 663b measures radial displacement again using strain measurements, and the linear variable displacement transduces (LVDT) 663 measure axial displacement of sample 630. All such measurements are made of sample 630 as it undergoes testing and evaluation in accordance with System 100 as described above. Thermocouples 666/668 are also housed within chamber 620 to report temperature. They interrelate through a temperature controller 901 which is a thermostat, typically within the heaters or chillers as discussed above.

Referring still to FIG. 10, various sensors are also positioned on the sub-system skids 300, 400, 500, 600, 700, and 800, as discussed above and shown in corresponding FIGS. 2, 3A, 4A, 5, 6A, 8, 9A-C. Thermocouples (for example, 339 and 390) again serve to measure temperature at each ones location in the system. They interrelate through a temperature controller 902 which is again a thermostat, typically within the heaters or chillers as discussed above. Pressure transducers (for example 341, 417, 423, 565, 744, and 832/833) serve to measure pressure again at the corresponding location of the specific pressure transducer, and flow meters 380 and 861 measure flow rates as discussed above.

All the data from the test chamber vessel and skid sensors are then sent to a computer or microprocessor 1200 which processes the data in accordance with the operative software to evaluate the performance of sample 630 under the test conditions. Stress and strain readings from various sensors as shown in FIG. 10 are manipulated to obtain displacement of the sample, both axially and radially.

$$\dot{M}_{upstream} = \dot{M}_{downstream} \text{ (pre-drilled state)}$$

$$\dot{M}_{upstream} = \dot{M}_{downstream} + \dot{M}_{core\ exchange} + \dot{M}_{exiting\ debris}$$
(drilled state)

Microprocessor 1200 compiles data streams generated by the various sensors set forth in FIG. 10 and discussed above. These data streams are processed in order to track sample 630 and associated fluid interactions and to study the behavior of sample 630. Such processing of data streams also provides dynamic control feedback for execution of the test and maintenance of testing parameters, such as fluid temperature. Such is possible since the sensors provide temperature feedback, stress/pressure measurements, strain/deformation measurements, and axial displacement. Such data steams may also be stored or re-analyzed in various ways depending on the needs of the operator consistent with this disclosure.

The foregoing invention has been described in terms of various embodiments. Modifications and alterations to these embodiments will be apparent to those skilled in the art in view of this disclosure. It is, therefore, intended that all such equivalent modifications and variations fall within the spirit and scope of the invention as claimed.

What is claimed is:

1. A system for simulating in situ subterranean formation conditions and testing and measuring the performance of a drilling or treating fluid on a core sample from the subterranean formation, the system comprising:
   a source of the fluid;
   a motor assembly to circulate the fluid within the system;
   a first pressure source to generate a pressure representative of the overburden pressure of the subterranean formation;
   a second pressure source to generate a substantially uniform lateral pressure representative of the pressure exerted on the pores of the sample from the subterranean formation;
   a third pressure source to generate a pressure representative of the confining pressure exerted laterally on the sample from the subterranean formation;
   a transfer assembly to impose substantially the same pressure on the fluid as generated by the first pressure source;
   a first measuring source to detect selected properties of the fluid prior to testing; and
   a test structure having a frame, a test chamber supported within the frame to support the sample, and a drilling assembly to drill a bore hole in the scruple using the fluid to circulate around a bit within the sample, wherein the test structure includes a header and a hollow rod member supported on the test chamber and in contact with the header, wherein the header is movable onto the hollow rod member to exert a mechanical load onto the sample supported within the test chamber to represent the overbearing pressure of the subterranean formation on the sample to subject the sample to substantially the same pressures as established by the first, second, and third pressure sources, wherein the drilling assembly comprises a drill stem extending through the hollow rod member, and further wherein the drilling assembly is capable of moving independently from the header.

2. The system according to claim 1, the system further comprising a second measuring source to detect selected properties of the fluid following testing.

3. The system according to claim 2 further comprising a processor to compare the results from the first measuring source and the second measuring source to determine the impact of the simulated drilling activity on the characteristics of the fluid and the impact of the fluid on the sample.

4. The system according to claim 3 further comprising a plurality of sensors to measure various properties of the sample.

5. The system according to claim 4 wherein the plurality of sensors comprises at least one sensor to measure radial strain of the sample.

6. The system according to claim 4 wherein the plurality of sensors comprises at least one load cell to measure axial displacement of the sample.

7. The system according to claim 1 wherein the motor assembly comprises a progressive cavity pump.

8. The system according to claim 1 wherein the overburdened pressure is between about 5,000 psi and about 30,000 psi.

9. The system according to claim 8 wherein the overburdened pressure is between about 15,000 psi and about 25,000 psi.

10. The system according to claim 1 further comprising at least one heater to heat the fluid to a predetermined temperature.

11. The system according to claim 10 wherein the predetermined temperature is between about 300° F. and about 450° F.

12. The system according to claim 11 wherein the predetermined temperature is between about 350° F. and about 425° F.

13. The system according to claim 12 wherein the predetermined temperature is about 400° F.

14. The system according to claim 1 wherein the pressure generated by the second pressure source is between about 5,000 psi and about 30,000 psi.

15. The system according to claim 14 wherein the pressure generated by the second pressure source is between about 15,000 psi and about 25,000 psi.

16. The system according to claim 15 wherein the pressure generated by the second pressure source is about 20,000 psi.

17. The system according to claim 1 wherein the pressure generated by the third pressure source is between about 5,000 psi and about 30,000 psi.

18. The system according to claim 17 wherein the pressure generated by the third pressure source is between about 15,000 psi and about 25,000 psi.

19. The system according to claim 18 wherein the pressure generated by the third pressure source is about 20,000 psi.

20. The system according to claim 1 wherein the second pressure source comprises at least one intensifier pump.

21. The system according to claim 1 wherein the third pressure source comprises at least one intensifier pump.

22. The system according to claim 1 wherein the transfer assembly comprises at least one accumulator.

23. The system according to claim 1 wherein the first measuring source comprises a Coriolis meter.

24. The system according to claim 1 wherein the second measuring source comprises a Coriolis meter.

25. The system according to claim 1, the system further comprising at least three heaters.

26. The system according to claim 1, the system further comprising at least five heaters.

27. The system according to claim 1 wherein the test chamber comprises a top plate, a cylindrical sleeve, and a bottom plate.

28. The system according to claim 1 wherein the frame further comprises:
   a base;
   at least two vertical members laterally restrained within the base;
   at least one rotary motor supported by the vertical members; and
   at least one gearbox connecting the rotary motor to at least one of the vertical members.

29. The system according to claim 1 wherein the test structure further comprises an inner chamber structure having a top plate, a substantially non-porous, compliant sleeve, and a bottom plate adapted to support the sample during testing.

30. A system for simulating in situ subterranean formation conditions and testing and measuring the performance of a drilling or treating fluid on a core sample from the subterranean formation, the system comprising:
   source fluid;
   a motor assembly to circulate the fluid within the system;
   a first pressure source to generate a pressure representative of an overburden pressure of the subterranean formation;

a second pressure source to generate a substantially uniform lateral pressure representative of the pressure exerted on the pores of the sample from the subterranean formation;

a third pressure source to generate a pressure representative of the confining pressure exerted laterally on the sample from the subterranean formation;

a transfer assembly to impose substantially the same pressure on the fluid as generated by the first pressure source;

a first measuring source to detect selected properties of the fluid prior to testing;

at least one heater to heat the fluid to a predetermined temperature;

a test structure having a frame, a test chamber supported within the frame to support the sample, and a drilling assembly to drill a bore hole in the sample using the heated fluid to circulate around a bit within the sample, wherein the test structure subjects the sample to substantially the same pressures as established by the first, second, and third pressure sources, the frame having a base, at least two vertical members laterally restrained within the base, at least one rotary motor supported by the vertical members, and at least one gearbox connecting the at least one rotary motor to at least one of the vertical members, wherein the test structure has a header releasably connected to the vertical members, and a rod member supported on the test chamber and in contact with the header, wherein activation of the at least one rotary motor and at least one gearbox causes rotational movement of the elongated members thereby lowering the header onto the rod member and exerting a mechanical load onto the sample supported within the test chamber to represent the overbearing pressure of the subterranean formation on the sample;

a second measuring source to detect selected properties of the fluid following testing; and a processor to compare the results from the first measuring source and the second measuring source to determine the impact of the simulated drilling activity on the characteristics of the fluid and the impact of the fluid on the sample.

31. A system comprising:

a core sample;

a source fluid representative of a drilling or treating fluid usable in a subterranean formation and in communication with the core sample;

a motor assembly to circulate the fluid within the system;

a first measuring source and a second measuring source to detect selected properties of the fluid;

a plurality of pressure sources to generate a pressure representative of the overburden pressure of the subterranean formation, a pressure representative of the pressure exerted on the pores of the core sample from the subterranean formation, and a pressure representative of the confining pressure exerted laterally on the core sample from the subterranean formation;

a test structure having a frame, a test chamber supported within the frame to support the core sample, and a drilling assembly to drill a bore hole in the core sample using the fluid to circulate around a bit within the core sample, wherein the test structure subjects the core sample to substantially the same pressures as established by the plurality of pressure sources, includes a header and a hollow rod member supported on the test chamber and in contact with the header, wherein the header is movable onto the hollow rod member to exert a mechanical load onto the core sample supported within the test chamber to represent the overbearing pressure of the subterranean formation on the core sample to subject the core sample to substantially the same pressures as established by the plurality of pressure sources and, wherein the drilling assembly comprises a drill stem extending through the hollow rod member, further wherein the drilling assembly is capable of moving independently from the header;

a plurality of sensors to measure various properties of the core sample during testing; and a processor to compare the results from the first measuring source and the second measuring source to determine the impact of the simulated drilling activity on the fluid, and to process data coming from said plurality of sensors to determine the impact of the simulated drilling on the core sample.

32. The system according to claim 31 wherein the plurality of sensors comprises at least one acoustical sensor.

33. The system according to claim 32 wherein the plurality of sensors comprises at least one sensor to measure radial strain of the core sample.

34. The system according to claim 32 wherein the plurality of sensors comprises at least one LVDT sensor.

35. The system according to claim 32 wherein the plurality of sensors comprises at least one load cell to measure axial displacement of the core sample.

36. The system according to claim 31 wherein the motor assembly comprises a progressive cavity pump.

37. The system according to claim 31 wherein the overburdened pressure generated is between about 5,000 psi and about 30,000 psi.

38. The system according to claim 37 wherein the overburdened pressure generated is between about 15,000 psi and about 25,000 psi.

39. The system according to claim 38 wherein the overburdened pressure generated is about 20,000 psi.

40. The system according to claim 31 wherein the pore pressure generated is between about 5,000 psi and about 30,000 psi.

41. The system according to claim 40 wherein the pore pressure generated is between about 15,000 psi and about 25,000 psi.

42. The system according to claim 41 wherein the pore pressure generated is about 20,000 psi.

43. The system according to claim 31 wherein the confining pressure generated is between about 5,000 psi and about 30,000 psi.

44. The system according to claim 43 wherein the confining pressure generated is between about 15,000 psi and about 25,000 psi.

45. The system according to claim 44 wherein the confining pressure generated is about 20,000 psi.

46. The system according to claim 31 wherein the pressure source which generates the pore pressure comprises at least one intensifier pump.

47. The system according to claim 31 wherein the pressure source which generates the confining pressure comprises at least one intensifier pump.

48. The system according to claim 31, the system further comprising a transfer assembly to impose substantially the same overburden pressure on the fluid as generated by at least one of the plurality of pressure sources, wherein the transfer assembly comprises at least one accumulator.

49. The system according to 31 wherein the first measuring source comprises a Coriolis meter.

50. The system according to claim 31 wherein the second measuring source comprises a Coriolis meter.

51. The system according to claim 31, the system further comprising at least three heaters.

52. The system according to claim 31, the system further comprising at least five heaters.

53. The system according to claim 31, the system further comprising at least one heater to heat the fluid to a predetermined temperature, wherein the predetermined temperature is between about 300° F. and about 450° F.

54. The system according to claim 53 wherein the predetermined temperature is between about 350° F. and about 425° F.

55. The system according to claim 54 wherein the predetermined temperature is about 400° F.

56. The system according to claim 31 wherein the test chamber comprises a top plate, a cylindrical sleeve, and a bottom plate.

57. The system according to claim 31 wherein the frame further comprises:
   a base;
   at least two vertical members laterally restrained within the base;
   at least one rotary motor supported by the vertical members; and
   at least one gearbox connecting the at least one rotary motor to at least one of the vertical members.

58. The system according to claim 31 wherein the test structure further comprises an inner chamber structure having a top plate, a rubber sleeve, and a bottom plate adapted to support the core sample during testing.

* * * * *

UNITED STATES PATENT AND TRADEMARK OFFICE
CERTIFICATE OF CORRECTION

Page 1 of 1

PATENT NO. : 10,845,354 B2
APPLICATION NO. : 16/367970
DATED : November 24, 2020
INVENTOR(S) : Joel Franklin Hugghins et al.

It is certified that error appears in the above-identified patent and that said Letters Patent is hereby corrected as shown below:

In the Claims

Column 21, Line 25:
Delete "scruple"; replace with --sample--

Signed and Sealed this
Twelfth Day of January, 2021

Andrei Iancu
*Director of the United States Patent and Trademark Office*